US011987832B2

(12) United States Patent
Manning et al.

(10) Patent No.: US 11,987,832 B2
(45) Date of Patent: *May 21, 2024

(54) ENDOGENOUS LIPASE FOR METAL REDUCTION IN DISTILLERS CORN OIL

(71) Applicant: POET Research, Inc., Sioux Falls, SD (US)

(72) Inventors: Andrew J. Manning, Sioux Falls, SD (US); Alex T. McCurdy, Sioux Falls, SD (US); Steven T. Bly, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/395,282

(22) Filed: Aug. 5, 2021

(65) Prior Publication Data

US 2022/0042049 A1 Feb. 10, 2022

Related U.S. Application Data

(60) Provisional application No. 63/062,135, filed on Aug. 6, 2020.

(51) Int. Cl.
| | |
|---|---|
| C12P 7/14 | (2006.01) |
| A01N 63/50 | (2020.01) |
| C12M 1/34 | (2006.01) |
| C12N 9/22 | (2006.01) |

(52) U.S. Cl.
CPC ..................................... *C12P 7/14* (2013.01)

(58) Field of Classification Search
CPC ..................... C12N 9/22; C12P 7/14
See application file for complete search history.

(56) References Cited

U.S. PATENT DOCUMENTS

| | | | |
|---|---|---|---|
| 1,737,402 A | 11/1929 | Ayres | |
| 2,510,379 A | 6/1950 | Christenson | |
| 2,510,402 A | 6/1950 | Johnston | |
| 2,762,780 A | 9/1956 | Kulakow | |
| 2,881,195 A | 4/1959 | Hayes | |
| 3,354,188 A | 11/1967 | Bock | |
| 4,049,686 A | 9/1977 | Ringers et al. | |
| 4,609,500 A | 9/1986 | Strecker | |
| 4,698,185 A | 10/1987 | Dijkstra et al. | |
| 4,713,155 A | 12/1987 | Arutjuanian et al. | |
| 5,208,054 A | 5/1993 | Torrii et al. | |
| 5,239,096 A | 8/1993 | Rohdenburg et al. | |
| 5,512,691 A | 4/1996 | Barnicki et al. | |
| 5,516,924 A | 5/1996 | van de Sande et al. | |
| 6,015,915 A | 1/2000 | Jamil et al. | |
| 6,033,706 A | 3/2000 | Silkeberg et al. | |
| 6,074,863 A | 6/2000 | Svendsen et al. | |
| 6,103,918 A | 8/2000 | Dahlen | |
| 6,407,271 B1 | 6/2002 | Deffense | |
| 6,426,423 B1 | 7/2002 | Copeland et al. | |
| 6,514,332 B2 | 2/2003 | Varnadoe et al. | |
| 6,743,930 B2 | 6/2004 | Li | |
| 6,764,542 B1 | 7/2004 | Lackey et al. | |
| 6,776,832 B2 | 8/2004 | Spence et al. | |
| 6,844,458 B2 | 1/2005 | Copeland et al. | |
| 6,924,381 B2 | 8/2005 | Dawson | |
| 7,122,216 B2 | 10/2006 | Copeland et al. | |
| 7,582,458 B2 | 9/2009 | Grichko | |
| 7,601,858 B2 | 10/2009 | Cantrell et al. | |
| 7,696,369 B2 | 4/2010 | Kellens et al. | |
| 7,713,727 B2 | 5/2010 | Dayton et al. | |
| 7,842,484 B2 | 11/2010 | Lewis | |
| 7,879,917 B2 | 2/2011 | Cheng et al. | |
| 7,893,115 B2 | 2/2011 | Cheng et al. | |
| 7,919,291 B2 | 4/2011 | Lewis et al. | |
| 8,008,516 B2 | 8/2011 | Cantrell et al. | |
| 8,076,123 B2 | 12/2011 | Chou | |
| 8,114,926 B2 | 2/2012 | Dupuis et al. | |
| 8,163,059 B2 | 4/2012 | Tran et al. | |
| 8,232,418 B1 | 7/2012 | Bilbie et al. | |
| 8,435,766 B2 | 5/2013 | Kellens et al. | |
| 8,476,047 B2 | 7/2013 | Burlew et al. | |

(Continued)

FOREIGN PATENT DOCUMENTS

| | | |
|---|---|---|
| BR | PI0704791 | 7/2009 |
| EP | 2656834 | 10/2013 |

(Continued)

OTHER PUBLICATIONS

Abdulkadir et al. (2017) Production and Refining of Corn Oil from Hominy Feed a By-Product of Dehuling Operation: ARPN Journal of Engineering an Applied Sciences 6(4):7 pages.
Back-End Value Enhanced through Patented Technology and Strategic Partnerships retrieved from www.valicor.com (5 pages).
Bailey (2010) "Novel Uses of Vegetable Oil in Asphalt Mixtures", Ph.D Thesis, U. of East London, UK, Sep. 2010) 366 pgs.
Bailey (2012) "The Use of Vegetable Oil as a Rejuvenator for Asphalt Mixtures", 5th Eurasphalt and Eurobitume Congress, Istanbul, (Jun. 13-15, 2012) 10 pgs.
Bailey (2012) "The Use of Vegetable Oil in Asphalt Mixtures, in the Laboratory and Field", 5th Eurasphalt and Eurobitume Congress, Istanbul, {Jun. 13-15, 2012) 12 pgs.

(Continued)

*Primary Examiner* — Maryam Monshipouri
(74) *Attorney, Agent, or Firm* — FisherBroyles, LLP; Cara L. Crowley-Weber; Cary Reeves

(57) ABSTRACT

Provided herein are compositions, methods, systems associated with propagation and fermentation, and co-products of biochemical production processes, for example, a DCO co-product resulting from converting oil containing grains into bio chemicals via fermentation in the presence of endogenous esterase. The DCO resulting from the processes exhibits lower metal ion content relative to a DCO obtained in the absence of endogenous fermentation with an esterase such as a lipase. The DCO is useful as a feedstock for the production of renewable diesel.

7 Claims, No Drawings

Specification includes a Sequence Listing.

(56) References Cited

U.S. PATENT DOCUMENTS

| | | | |
|---|---|---|---|
| 8,608,845 B2 | 12/2013 | Naidoo et al. | |
| 8,637,290 B2 * | 1/2014 | O'Donoghue | C12P 7/6481 |
| | | | 435/197 |
| 8,702,819 B2 | 4/2014 | Bootsma | |
| 8,759,044 B2 | 6/2014 | Dicosimo et al. | |
| 8,765,425 B2 | 7/2014 | Dicosimo et al. | |
| 8,765,985 B2 | 7/2014 | Hora et al. | |
| 8,808,445 B2 | 8/2014 | Coe | |
| 8,901,330 B2 | 12/2014 | Doyle et al. | |
| 8,962,059 B1 | 2/2015 | Froderman et al. | |
| 9,045,712 B2 | 6/2015 | Dayton et al. | |
| 9,061,987 B2 | 6/2015 | Bootsma | |
| 9,109,179 B2 | 8/2015 | Cowin et al. | |
| 9,139,803 B2 | 9/2015 | Redford | |
| 9,144,758 B2 | 9/2015 | Wang et al. | |
| 9,228,211 B2 | 1/2016 | Soe et al. | |
| 9,255,239 B1 | 2/2016 | Wiese | |
| 9,290,728 B2 | 3/2016 | Bootsma | |
| 9,340,749 B1 | 5/2016 | Kozyuk et al. | |
| 9,388,100 B2 | 7/2016 | Redford | |
| 9,416,274 B2 | 8/2016 | Frank | |
| 9,453,180 B2 | 9/2016 | Kozyuk et al. | |
| 9,481,794 B2 | 11/2016 | Cox et al. | |
| 9,481,853 B2 | 11/2016 | Gordon et al. | |
| 9,534,182 B1 | 1/2017 | Ballard | |
| 9,534,184 B2 | 1/2017 | Thompson et al. | |
| 9,556,399 B2 | 1/2017 | Kozyuk et al. | |
| 9,617,425 B1 | 4/2017 | Moriyasu et al. | |
| 9,695,449 B2 | 7/2017 | Bootsma | |
| 9,765,280 B2 | 9/2017 | Kurth et al. | |
| 9,783,458 B2 | 10/2017 | Martin | |
| 1,247,782 A1 | 11/2017 | Ayres | |
| 9,896,643 B2 | 2/2018 | Redford | |
| 9,961,916 B2 | 5/2018 | Arhancet et al. | |
| 10,087,397 B2 | 10/2018 | Phillips et al. | |
| 10,113,187 B2 | 10/2018 | Bushong et al. | |
| 10,167,390 B2 | 1/2019 | Cox | |
| 10,323,148 B1 | 6/2019 | Brewster et al. | |
| 10,526,564 B2 | 1/2020 | Phillips et al. | |
| 10,526,623 B2 | 1/2020 | Bootsma | |
| 10,584,304 B2 | 3/2020 | Schnell et al. | |
| 10,604,776 B2 * | 3/2020 | McCurdy | C12P 7/06 |
| 10,711,221 B2 | 7/2020 | Lamprecht et al. | |
| 10,781,464 B2 | 9/2020 | Yoshida et al. | |
| 10,815,430 B2 * | 10/2020 | Gutierrez | C10G 3/50 |
| 10,815,506 B2 | 10/2020 | Rancke-Madsen et al. | |
| 10,851,327 B2 | 12/2020 | Urban et al. | |
| 10,899,928 B2 | 1/2021 | McCurdy et al. | |
| 11,008,531 B2 | 5/2021 | Lamprecht et al. | |
| 11,104,922 B2 | 8/2021 | McCurdy et al. | |
| 2004/0063184 A1 | 4/2004 | Grichko | |
| 2006/0041152 A1 | 2/2006 | Cantrell et al. | |
| 2006/0089429 A1 | 4/2006 | Buras et al. | |
| 2006/0215483 A1 | 9/2006 | Helf | |
| 2008/0006889 A1 | 3/2008 | Palacios | |
| 2008/0146851 A1 | 6/2008 | Schonemann et al. | |
| 2008/0176298 A1 | 7/2008 | Randhava et al. | |
| 2008/0314294 A1 | 12/2008 | White et al. | |
| 2009/0137705 A1 | 5/2009 | Faucon Dumont et al. | |
| 2009/0306419 A1 | 12/2009 | Myong et al. | |
| 2010/0034586 A1 | 2/2010 | Bailey et al. | |
| 2010/0058649 A1 | 2/2010 | Bailey et al. | |
| 2010/0125356 A1 | 5/2010 | Shkolnik | |
| 2010/0191360 A1 | 7/2010 | Napadensky | |
| 2011/0086149 A1 | 4/2011 | Bootsma | |
| 2011/0093965 A1 * | 4/2011 | O'Donoghue | C12P 7/649 |
| | | | 435/254.11 |
| 2012/0060722 A1 | 3/2012 | Montpeyrous et al. | |
| 2012/0245370 A1 | 9/2012 | Sheppard et al. | |
| 2013/0157324 A1 | 6/2013 | Dicosimo et al. | |
| 2014/0230693 A1 | 8/2014 | Gonzalez et al. | |
| 2014/0371895 A1 | 12/2014 | Sadusk | |
| 2015/0230488 A1 | 8/2015 | de Man et al. | |
| 2015/0291923 A1 | 10/2015 | Bootsma | |
| 2016/0145650 A1 | 5/2016 | Lewis et al. | |
| 2016/0185044 A1 | 6/2016 | Leonard | |
| 2016/0250810 A1 | 9/2016 | Lynch | |
| 2017/0022364 A1 | 1/2017 | Cox | |
| 2017/0066995 A1 | 3/2017 | Borst et al. | |
| 2017/0107449 A1 | 4/2017 | Hruschka et al. | |
| 2017/0107452 A1 | 4/2017 | Sarai et al. | |
| 2017/0145642 A1 | 5/2017 | Swanosn | |
| 2017/0283838 A1 | 10/2017 | Bootsma | |
| 2017/0304894 A1 | 10/2017 | Buller | |
| 2018/0273988 A1 | 9/2018 | Lewis et al. | |
| 2018/0340067 A1 | 11/2018 | McCurdy et al. | |
| 2018/0340068 A1 | 11/2018 | McCurdy et al. | |
| 2018/0340197 A1 | 11/2018 | McCurdy et al. | |
| 2019/0249109 A1 | 8/2019 | Lamprecht et al. | |
| 2019/0376002 A1 | 12/2019 | Urban et al. | |
| 2020/0063168 A1 | 2/2020 | Bootsma | |
| 2020/0131403 A1 | 4/2020 | McCurdy | |
| 2020/0165642 A1 | 5/2020 | McCurdy et al. | |
| 2020/0299610 A1 | 9/2020 | Marques de Lima | |
| 2021/0032564 A1 | 2/2021 | Urban et al. | |
| 2021/0332244 A1 | 10/2021 | McCurdy et al. | |

FOREIGN PATENT DOCUMENTS

| | | |
|---|---|---|
| EP | 2689006 | 1/2014 |
| EP | 2264157 | 5/2014 |
| GB | 481580 | 3/1938 |
| GB | 766394 | 1/1957 |
| GB | 1065720 | 4/1967 |
| GB | 1562380 | 3/1980 |
| JP | 005154467 | 6/2005 |
| JP | 4257188 | 4/2009 |
| WO | WO 8802775 | 4/1988 |
| WO | WO 9323508 | 11/1993 |
| WO | WO 9421762 | 9/1994 |
| WO | WO 9801518 | 1/1998 |
| WO | WO 2004007654 | 1/2004 |
| WO | WO 2004081193 | 9/2004 |
| WO | WO 2008061120 | 5/2008 |
| WO | WO 2009120419 | 10/2009 |
| WO | WO 2010053244 | 5/2010 |
| WO | WO 2010077141 | 7/2010 |
| WO | WO 2012109221 | 8/2012 |
| WO | WO 2012129548 | 9/2012 |
| WO | WO 2014037008 | 3/2014 |
| WO | WO 2014158011 | 10/2014 |
| WO | WO 2015168020 | 11/2015 |
| WO | WO 2015181308 | 12/2015 |
| WO | WO 2016003465 | 1/2016 |
| WO | WO 2016178676 | 11/2016 |
| WO | WO 2018024654 | 2/2018 |
| WO | WO 2018031540 | 2/2018 |
| WO | WO 2018217198 | 11/2018 |
| WO | WO 2018218033 | 11/2018 |
| WO | WO 2019069992 | 4/2019 |

OTHER PUBLICATIONS

Barros et al. (2010) "Seed lipases: sources, application and properties—a review" Brazilian J of Chem Engineering 27(1):15-29.

Bennert et al. (2016) "Fatigue Performance of Re-Refined Engine Oil Bottoms (REOB) Modified Asphalt—A Laboratory Study", 95th Annual Transportation Research Board Meeting.

Brothers et al. (2018) "Free fatty-acid generation and lipid oxidation during dry-grind corn ethanol fermentation" J American Oil Chem Soc 95(12):1521-1533.

Cesarini et al. (2015) "Moving towards a competitive fully enzymatic biodiesel process" Sustainability 7:7884-7903.

Corn Oil, Retrieved from https://com.org/resources/?fwp_resource_type=pdf&fwp_search=corn%20oil, 2006 24 pages.

D'Amore et al. (1990) "A Study of Ethanol Tolerance in Yeast", Critical Reviews in Biotechnology 9:4.

D'Amore et al. (1987) "Ethanol tolerance of yeast" Enzyme and Microbial Technology 9:6-17.

Defoamer Retrieved from https://en.wikipedia.org/wiki/defoamer on May 30, 2019, 5 pages.

(56) References Cited

OTHER PUBLICATIONS

European Search Report for the related Application No. 18806452.1, PCT/US201803441, dated Feb. 1, 2021, 9 pages.
Friedrich et al. (1984) "Properties and processing of corn oils obtained by extraction with supercritical carbon dioxide" JAOCS 61:12-15.
Gibbons et al. (2009) "Integrated biorefineries with engineered microbes and high-value co-products for profitable 2 biofuels production" In Vitro Cellular & Development Biology Plant 45(3):218-228, XP055270849, US ISSN: 1054-5476, DOI: 10.1007/s11627-009-9202-1, 10 pages.
Golalipour (2013) "Investigation of the Effect of Oil Modification on Critical Characteristics of Asphalt Binders", PhD Dissertation, U. of Wisconsin—Madison, [Online]. Retrieved from the Internet: <URL: http://www.asphaltinstitute.org/wp-content/uploads/Thickness Mix/PhDDissertationDocument-Final-AG2.pdf>, 204 pgs.
Hughes et al. (2011) "Production of Candida antarctica lipase B gene open reading frame using automated PCR gene assembly protocol on robotic workcell and expression in an ethanologenic yeast for use as resin-bound biocatalyst in biodiesel production" Journal of the Association for Lab. Automation 16(1):17-37.
International Search Report and Written Opinion from Application Serial No. PCT/US2017/034262, dated Mar. 23, 2018 7 pages.
International Search Report and Written Opinion for Application Serial No. PCT/US2018/034410, dated Jan. 17, 2019, 6 pages.
International Search Report for Application No. PCT/US2019/036578 dated May 14, 2019 6 pages.
International Search Report for Application No. PCT/US2019/036578 dated Oct. 11, 2019 5 pages.
Japir et al. "Separation of free fatty acids from high free fatty acid crude palm oil using short path distillation" 2016 UKM FEST Postgraduation Collegium AIP Conf. Proc. 1784 03001-1-030001-8 9 pages.
Layfield et al., (2015) "What Brewers Should Know About Viability, Vitality, and Overall Brewing Fitness: A Mini-Review" Master Brew. Assoc. Am. 52:3-12.
LCI Corporation "Short Path Evaporation" retrieved from https://lcicorp.com/short_path_evaporators/short_path_evaporator 2 pages.
Meng et al. (2011) "Two-step synthesis of fatty acid ethyl ester from soybean oil catalyzed by Yarrowia lipolvtica lipase", Biotechnology for Biofuels 4(6):9 pages.
Micro-fine silica treated 1 with an organic silicone compound, DUMACIL® 100 FGK, Elementis Specialties Apr. 2017 1 page.
Mogawer et al. (2013) "Evaluating the effect of rejuvenators on the degree of blending and performance of high RAP, RAS, and RAP/RAS mixtures" Road Materials and Pavement Design 14(2):29 pages.
Moghaddam (2016) "The use of rejuvenating agents in production of recycled hot mix asphalt: A systematic review" Construction and Building Materials 114:805-816.
Moreau et al. (2010) "Changes in Lipid Composition During Dry Grind Ethanol Processing of Corn" Journal of the American Oil Chemist's Society 88:9 pages.
Oliveira et al. (1991) "Production and extracative biocatalysis of ethanol using microencapsulated yeast cells and lipase system" J of Chem Tech & Biotech 52(2):1231-1238.
Saini et al. (2018) Carotenoid extraction methods: A review of recent developments Food Chemistry 240:90-103.
Seidel et al. (2014) "Rheological characterization of asphalt binders modified with soybean fatty acids" Construction and Building Materials 53:324-332.
Skaliotis (2011) "Short Path to Premium quality oils" Food Marketing and Technology 23-26.
Standard Reapproved Test Method 2001, 2 for pages. Foaming Properties of Surface-Active Agenst1, Designation: D 1173-53.
Standard Test Method for Foaming Properties of Surface-Active Agents1, Designation D 1173-53 Reapproved 2001 2 pages.
Tesfaw et al. (2014) "Current trends in bioethanol production by *Saccaromyces cerevisiae*: substrate, inhibitor reduction, growth variables, coculture and immobilization" International Scholarly Research Notices pp. 1-11.
Van Den Berg et al. (2013) "Simultaneous clostridial fermentation, lipase-catalyzed esterification, and ester extraction to enrich diesel with butyl butyrate" Biotechnology and Bioenaineerina 11(1): 6 pages.
Winkler et al. (2007) "Phytosterol and Tocopherol Components in Extracts of Corn Distiller's Dried Grain" J. Aqric. Food Chem. 55(16):6482-6486.
Winkler-Moser (2011) "Composition and oxidative stability of crude oil extracts of corn germ and distillers Grains" Industrial Crops and Products 33:572-578.
Winkler-Moser et al. (2009) "Antioxidant Activity of Phytochemicals from Distillers Dried Grain Oil" Journal of the American Oil Chemist's Society 86:1073-1082.
Yusoff et al. (2014) "Comparison of fatty acid methyl and ehtyl esters as biodiesel base stock: a review on processing and production requirements" J Am Oil Chem Soc 91:525-531.
Zaumanis (2013) "Use of Rejuvenators for Production" VIII International Baltic Road Conference 10 pgs.
Zaumanis et al. (2014) "Influence of six rejuvenators on the performance properties of Reclaimed Asphalt Pavement (RAP) binder and 100% recycled asphalt mixtures", Construction and Building Materials 71: 14 pages.
Oliveira et al. (1998) "In situ recovery of ethanol by extraction and enzymatic esterification" Med. Fac. Fandouww 63:1231-1238.

* cited by examiner

ENDOGENOUS LIPASE FOR METAL REDUCTION IN DISTILLERS CORN OIL

RELATED APPLICATIONS

This application claims the benefit of U.S. Provisional application No. 63/062,135 titled "Endogenous Lipase for Metal Reduction in Distillers Corn Oil" filed Aug. 6, 2020 which is incorporated herein by reference.

TECHNICAL FIELD

Provided herein are methods, compositions, and systems for propagation and fermentation, particularly in large scale operations for production of ethanol dried distillers grain, and distillers corn oil.

SEQUENCE LISTING

An official copy of the sequence listing is submitted concurrently with the specification electronically via EFS-Web as an ASCII formatted sequence listing with a file name of PT-150-US02_ST25.TXT, a creation date of Aug. 5, 2021, and a size of about 80.9 kilobytes. The sequence listing contained in this ASCII formatted document is part of the specification and is herein incorporated by reference in its entirety.

BACKGROUND

Ethanol can be produced from grain-based feedstocks (e.g. corn, sorghum/milo, barley, wheat, soybeans, etc.), from sugar (e.g. sugar cane, sugar beets, etc.), or from cellulosic biomass (e.g. lignocellulosic feedstocks, such as switchgrass, corn cobs and stover, wood or other plant material).

Conventional ethanol plants utilize corn as a feedstock and ethanol is produced from the starch within the corn. Corn kernels are cleaned and milled to prepare starch-containing material for processing. The starch-containing material is slurried with water and liquefied to promote saccharification and fermentation. Saccharification is the conversion of starch into sugar (e.g. glucose) and fermentation is the conversion of sugar into ethanol by an ethanologen (e.g. yeast). Fermentation yields a liquid component (ethanol, water, and soluble components) and a solids component (unfermented particulate matter). The fermentation product is distilled and dehydrated into ethanol. The residual matter or whole stillage contains water, soluble components, oil, syrup, and unfermented solids. The solids can be dried into dried distillers' grains (DDGs) and sold as animal feed product. Similarly, the other products can also be recovered and utilized such as oil for use as renewable diesel.

SUMMARY

Corn oil produced as a by-product of commercial ethanol fermentation, distillers corn oil (DCO), may contain enhanced levels of metal, which are detrimental for producing renewable diesel. Lipase treatment during fermentation greatly reduces the metal content, also referred to herein as "metal ion content", of DCO.

Provided herein are compositions, methods, systems associated with propagation and fermentation, and co-products of biochemical production processes, for example, a DCO co-product resulting from converting oil containing grains into bio chemicals via fermentation. The DCO is useful as a feedstock for the production of renewable diesel.

Provided herein are compositions comprising a primary feedstock, yeast, an esterase-producing organism, and water. The primary feedstock comprises the sugar source for propagation and fermentation by the microorganisms.

Provided herein are methods of reducing metal content in DCO produced as a co-product of ethanol production by utilizing an esterase-producing microorganism in propagation, fermentation, and/or in a side-tank propagation. The methods comprise (a) combining a feedstock, an ethanologen (e.g. yeast), an esterase-producing microorganism, and water in a propagator, side-tank, and/or fermenter; and (b) fermenting the feedstock. In some aspects, the esterase-producing microorganism is a yeast or bacteria. In some aspects, the ethanologen is also an esterase-producing organism (e.g. the ethanologen is able to produce both ethanol and esterase).

In some embodiments provided herein, the esterase-producing microorganism is genetically modified to produce a carboxylic esterase (e.g. lipase).

In some embodiments provided herein, the esterase-producing microorganism is genetically modified to produce a CALB lipase.

Provided herein are methods of producing DCO. The methods comprise: (a) inoculating a feedstock: (i) with a combination of a first microorganism for fermentation of the feedstock, i.e. an ethanologen, and a second microorganism for producing lipase; (ii) with a yeast for fermentation, i.e. an ethanologen or fermentation yeast, of the feedstock, wherein the yeast is genetically modified to produce lipase; or (iii) with a yeast strain for fermentation of the feedstock, i.e. an ethanologen, wherein the feedstock contains starch from a genetically modified plant engineered to produce lipase; and (b) fermenting the feedstock to produce ethanol and DCO.

In some aspects, step (a)(i) includes inoculating a feedstock in a propagation tank or a fermentation tank with the ethanologen and the second microorganism.

In some aspects, step (a)(i) includes inoculating a feedstock in a first propagation tank with the ethanologen and inoculating a feedstock in a second propagation tank (side tank propagation) with the second microorganism. In some aspects, step (b) further comprises fermenting contents obtained from the first propagation tank with contents obtained from the second propagation tank in the presence of feedstock for ethanol production.

In some aspects, step (a)(i) includes inoculating a feedstock in a fermentation tank with the ethanologen and inoculating a feedstock in a propagation tank (side tank propagation) with the second microorganism, and wherein step (b) further comprises adding the contents obtained from the propagation tank to the fermentation tank and fermenting feedstock for ethanol production.

In some aspects, step (a)(iii) includes a feedstock containing starch from a genetically modified plant engineered to produce lipase. The genetically modified plant can be, for example, corn, soybean, cottonseed, sunflower seed, canola, rapeseed, or peanut. Corn is used throughout the disclosure as an exemplary plant modified to produce lipase, such that the feedstock obtained from the corn plant contains sufficient levels of lipase useful in the processes and compositions provided herein. However, it is understood that any plant useful as a feedstock and genetically modified to produce lipase will be useful in the processes and compositions provided herein.

Propagation and/or fermentation with endogenously produced esterases, e.g. lipases, DCO with certain desirable properties. In some aspects, the DCO exhibits decreased levels of cationic metals ($Na^+$, $K^+$, $Mg^{2+}$, $Ca^{2+}$, etc.) relative to the levels of cationic metals present in DCO produced in the absence of a lipase-producing microorganism, yeast, or plant. In some aspects, the DCO exhibits decreased soap content and higher oil yield relative to the soap content in DCO produced in the absence of a lipase-producing microorganism, yeast, or plant. In some aspects, the DCO exhibits decreased viscosity relative to the viscosity of a DCO produced in the absence of a lipase-producing microorganism, yeast, or plant. In some aspects, the DCO comprises increased FAEE/decreased FFA relative to the FAEE/FFA content of a DCO produced in the absence of a lipase-producing microorganism, yeast, or plant. In some aspects, FAEE is increased anywhere from 1 to 5× and FFA are decreased anywhere from 1 to 5×, relative to the FAEE and FFA content of a DCO produced in the absence of a lipase-producing microorganism, yeast, or plant. In some aspects, FAEE is increased and FFA are decreased in a 1:1 ratio, relative to the FAEE and FFA content of a DCO produced in the absence of a lipase-producing microorganism, yeast, or plant. The change in FAEE/FFA content correlates with the decrease in metal ions content, but not necessarily in a linear or 1:1 fashion.

The lipase endogenous to the plant used as feedstock, i.e. a crop plant genetically modified to produce lipase or another esterase useful herein, e.g. corn used as feedstock, or the lipase produced by the microorganism in the propagation or fermentation, is present in the fermentation broth in an amount equivalent to about 0.01 to about 1.00 LU/g dry solids (DS); about 0.0001% to about 0.0300% w/w DS; about 0.02% to about 0.5% w/w corn oil; or about 1 L to about 100 L in a 550,000 gal fermentation vat. In some aspects, the lipase produced is present in an amount sufficient to reduce metal ion content in DCO to less than about 10 ppm. In some aspects, the lipase produced is present in the fermentation in an amount sufficient to reduce FFA content in DCO to less than about 15% relative to a fermentation in the absence of a lipase-producing microorganism, yeast, or plant. In some aspects, the lipase produced is present in the fermentation in an amount sufficient to reduce metal ion content in DCO by at least about 10% to about 100%, e.g. at least about 10% to about 90%, at least about 20% to about 90%, at least about 30% to about 90%, at least about 40% to about 90%, at least about 50% to about 90%, at least about 60%, at least about 70%, at least about 80%, at least about 90%, or about 100%, relative to a fermentation in the absence of a lipase-producing microorganism, yeast, or plant.

In some embodiments, as provided in 1(a)(i), the ethanologen is S. cerevisiae and the second microorganism is a genetically modified yeast engineered to produce lipase. The lipase produced by the second yeast is present in the fermentation in an amount sufficient to reduce metal ion content in DCO by at least about 10% to at about 100% relative to a fermentation in the absence of a lipase-producing microorganism, yeast, or plant.

In some embodiments, as provided in 1(a)(i), the ethanologen is S. cerevisiae and the second microorganism is a bacteria engineered to produce lipase. The lipase produced by the bacteria is present in the fermentation in an amount sufficient to reduce metal ion content in DCO by at least about 10% to about 100% relative to a fermentation in the absence of a lipase-producing microorganism, yeast, or plant.

In some embodiments, as provided in 1(a)(ii), the yeast is S. cerevisiae. In some aspects, the lipase produced by the yeast is present in the fermentation in an amount equivalent to about 0.03 to about 0.70 LU/g dry solids (DS). In some aspects, the lipase produced by the yeast is present in the fermentation in an amount sufficient to reduce metal ion content in DCO by at least about 10% to about 100% relative to a fermentation in the absence of a lipase-producing microorganism, yeast, or plant.

Provided herein are compositions for commercial production of ethanol. In some embodiments, the composition comprises two microorganisms: an ethanologen which is a yeast strain and a second microorganism which is a yeast strain or bacteria genetically modified to produce lipase under conditions for ethanol production. In some aspects, the ethanologen is S. cerevisiae. In some aspects, the second microorganism is a bacteria. In some aspects, the second microorganism is a yeast strain. In some aspects, the second microorganism is S. cerevisiae. In some embodiments, the composition comprises one microorganism: an ethanologen, such as yeast strain for fermentation of a feedstock but which is genetically modified to produce lipase under conditions for ethanol production. In some embodiments, the composition comprises an ethanologen, such as a yeast strain for fermentation of a feedstock under conditions for ethanol production, and ground corn obtained from a genetically modified plant which produces an esterase such as lipase.

The conditions for ethanol production are selected from the group consisting of:
(i) anaerobic fermentation;
(ii) fermentation solids content of at least about 20%;
(iii) a pH of about 4.0 to about 5.0; and
(iv) a temperature of about 25° C. to about 37° C., or about 30° C. to about 34° C.

Provided herein are fermenters comprising water, feedstock, an ethanologen, and a second microorganism which is a yeast strain or bacteria genetically modified to produce lipase under conditions for ethanol production.

Also provided herein are fermenters comprising water, feedstock, and an ethanologen such as a yeast strain which is genetically modified to produce lipase under conditions for ethanol production.

Also provided herein are fermenters comprising water, an ethanologen, such as a yeast strain for fermentation of a feedstock under conditions for ethanol production, and ground feedstock obtained from a genetically modified plant which produces an esterase such as lipase. The genetically modified plant can be corn, soybean, cottonseed, sunflower seed, canola, rapeseed, or peanut.

Provided herein are methods of producing DCO as a by-product of fermentation associated with ethanol production. In some aspects, the method comprises: (a) inoculating a feedstock with a combination of two yeast strains, wherein the first yeast strain is an ethanologen and the second yeast strain produces lipase; and (b) fermenting the feedstock to produce ethanol and DCO, wherein the metal ions content in the DCO is decreased by at least about 10% relative to a DCO obtained as the by-product of fermentation in the absence of a lipase producing yeast. In some aspects, the ethanol titer is unchanged relative to the same fermentation performed in the absence of the lipase expressing yeast strain.

Provided herein are methods of producing DCO. The methods comprise providing a first composition comprising water and ground corn; inoculating the first composition with: (i) a combination of a first yeast for fermentation of the ground corn, i.e. an ethanologen or fermentation yeast, and a second yeast engineered to produce lipase; or (ii) an ethanologen genetically modified to produce lipase; under conditions to form a second composition comprising oil, wherein the lipase produced is sufficient to reduce metal ion content in DCO; and isolating DCO from the second composition, wherein the metal ions content in the DCO is decreased relative to a DCO produced in the absence of a lipase producing yeast.

Provided herein are methods of producing DCO. The methods comprise providing a first composition comprising water and ground corn, wherein the ground corn comprises lipase, or is sourced from GMO corn expressing lipase; inoculating the first composition with yeast and fermenting the first composition under conditions to form a second composition comprising oil; and isolating DCO from the second composition, wherein the metal ions content in the DCO is decreased by at least about 10% relative to the metal ions content in DCO produced in the absence of ground corn comprising lipase.

In some aspects, the methods above further comprise breaking an emulsion comprising corn oil and isolating the oil to obtain DCO useful as a renewable diesel feedstock containing 10 ppm, 9 ppm, 8 ppm, 7 ppm, 6 ppm, 5 ppm, 4 ppm, 3 ppm, 2 ppm, 1 ppm, etc., metal ions.

Provided herein is a composition for ethanol production comprising ground corn, water, and *S. cerevisiae*, wherein the *S. cerevisiae* is genetically modified to produce lipase. In some aspects, the *S. cerevisiae* comprises a nucleotide sequence encoding a polypeptide selected from the group consisting of SEQ ID NOs: 1-27.

Provided herein is a composition for ethanol production comprising ground corn, water, and *S. cerevisiae*, wherein the ground corn comprises lipase in an amount sufficient to reduce metal ion content in distillers corn oil. In some aspects, the ground corn is obtained from a plant which is genetically modified to express lipase.

DESCRIPTION

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All patents, applications and non-patent publications mentioned in this specification are incorporated herein by reference in their entireties.

Industrial fermentation involves the breakdown of a feedstock by one or more microorganisms, e.g. yeast and/or bacteria, into one or more products. In addition to the feedstock, other nutrients may be provided to the organism to facilitate the fermentation. For example, a traditional ethanol fermentation process utilizes grain-based feedstocks (e.g., corn, sorghum/milo, barley, wheat, etc.), or other sugar sources (e.g., sugar cane, sugar beets, etc.). Enzymes, whether endogenous to the grain, added to the fermenter, or produced by yeast, convert components of the feedstock into simple sugars. Yeast, acting subsequent to or simultaneously with the enzymes, convert the simple sugars to ethanol and carbon dioxide.

In a typical ethanol production plant, corn, or other suitable primary feedstock is ground for fermentation. The entire corn kernel can be ground for fermentation, or the corn kernel may be fractionated into its component parts, and only the starchy endosperm ground for use in fermentation. Any suitable feedstock, subjected to virtually any suitable pretreatment, can be used in the methods and compositions provided herein.

The ground corn or other primary feedstock may be combined with water to form a slurry, and the pH of the slurry mixture may be adjusted as needed. A microorganism, for example, a yeast such as *S. cerevisiae*, is added. The yeast is selected to provide rapid growth and fermentation rates in the presence of high temperature and high ethanol levels. The amount of yeast starter employed is selected to effectively produce a commercially significant quantity of ethanol in a suitable time, e.g., less than 75 hours or less than 88 hours.

Yeast can be added to the fermentation by any of a variety of methods known for adding yeast to fermentation processes. Other desired components can be added to the fermenter, including certain enzymes which produce monomeric sugars from polymeric sugars (e.g. glucose from starch) in the fermentable solids for simultaneous saccharification and fermentation (SSF). These enzymes can be commercially sourced, may be present in the feedstock (genetically modified corn, for example), or may be expressed by the yeast. Exemplary enzymes include glucoamylase and alpha-amylase. Alternatively, saccharification can be performed separate from fermentation.

In some aspects, a fermenter contains a solids concentration of about 20% to about 50%, for example about 30% to about 40%, about 31%, about 32%, about 33%, about 34%, or about 35%. Maintaining overall fermenter solids concentrations within a specified range is useful for maximizing fermentability and ethanol production.

The slurry can be held at specified temperatures to facilitate the production of ethanol for a determined period of time. Fermenting can include contacting a mixture including sugars from the reduced plant material (e.g., fractionated plant material) with yeast under conditions suitable for growth of the yeast and production of ethanol. During fermentation, the yeast converts the sugars (e.g. glucose) to ethanol and carbon dioxide, and between the enzymatic production of sugars (e.g. glucose) and the fermentation process, sugars (e.g. glucose) may be maintained in the system at a low steady state. After fermentation, further treatment and/or distillation is performed to recover the ethanol, distillers corn oil (DCO), carbon dioxide, dried distillers grains (DDG), and/or other co-products.

The term "DCO" can be used generically to describe the oil co-product of a corn-to-ethanol process, including the oil present in, e.g., an emulsion in stillage and the isolated oil obtained by separating the oil from aqueous components of stillage, e.g., by breaking an emulsion and separating the aqueous phase. As used herein, DCO is the resulting corn oil after it has been recovered from the aqueous components.

DCO may contain levels of metal content ($Na^+$, $K^+$, $Mg^{2+}$, $Ca^{2+}$, etc.), which are detrimental to downstream processes. For example, metals in DCO may deactivate catalysts used in making renewable diesel.

The term "crude DCO" refers to distillers corn oil which has not been subjected to a refining process, i.e., distillation, deodorization, bleaching, etc. Refining can include a water or acid degumming step or chemical refining. The resulting gums or soap stock can be removed by centrifugation and/or other separation technology. These methods can be performed alone or in combination with a bleaching step to act as a pretreatment step to facilitate removal of metals from the oil prior to conversion to renewable diesel. The refining process can also lower the free fatty acid content (FFA), the moisture content, the insolubles content and/or the unsaponifiables content.

Triglycerides are the main constituent of vegetable fat and are esters having a glycerol backbone with three fatty acids attached to it. Similarly, diglycerides and monoglycerides are esters of glycerol with two and one fatty acids linked, respectively. Fatty acids may be separated from the glycerol backbone to become non-esterified fatty acids, i.e. free fatty acids (FFAs), such that a vegetable oil, depending on its source and processing, may have from a relatively low level to a relatively high level of FFAs; e.g. from 0 to greater than 20% FFA. As used herein, the term FFA refers to an unesterified fatty acid, or more specifically, a fatty acid having a carboxylic acid head and a saturated or unsaturated unbranched aliphatic tail (group) of about 4 to about 28 carbons. FFAs may be esterified with other alcohols to form a fatty acid ester. For example, a fatty acid methyl ester (FAME) is fatty acid esterified with methanol and a fatty acid ethyl ester (FAEE), is a fatty acid esterified with ethanol.

It has been determined and disclosed herein that addition of an endogenous esterase, i.e. an esterase-producing microorganism, to propagation and/or fermentation (including a side-tank propagation) can be beneficial to recovery of DCO having decreased metal ion content. As such, provided herein are compositions, methods, and systems for propagation and fermentation utilizing an esterase-producing microorganism.

While not wishing to be bound by theory, it is thought that fermentation with endogenous esterase, e.g. lipase, reduces metal ion content by decreasing FFA content and increasing FAEE content of the corn oil. The reduction in FFA reduces the opportunity for metal soaps to form e.g. when pH is increased during biorefinery processes e.g. when breaking an emulsion to separate corn oil from an aqueous stream. Some of these metal soaps will segregate with the oil during centrifugation. By limiting soap formation, fewer soaps, and thus fewer metal ions, segregate with the oil resulting in a lower metals content in the oil. The metal ions are instead dissolved in the aqueous stream and cleanly separate from the oil during centrifugation.

A yeast or bacteria that naturally produces lipase can be used in the methods, systems, and compositions provided herein. However, a yeast or bacteria can be genetically engineered to produce lipase. Exemplary bacteria which can be engineered to produce lipase include, but are not limited to *Escherichia coli*, *Bacillus* spp (several species), and *Pseudomonas* spp (several species). Exemplary yeast which can be engineered to produce lipase include, but are not limited to, *Candida boidinii*, *Pichia pastoris*, and *Saccharomyces cerevisiae*. Yeast or bacteria can be genetically engineered to produce an esterase, for example, a lipase according to any one of SEQ ID NOs: 1-27. Promoters are chosen which control the level of the enzyme produced by the cell, and in this case, tightly regulated or low expressing promotors are chosen to maintain esterase production at the desired level necessary to achieve a decreased metal ion content in the DCO.

In some embodiments, the esterase is a newly engineered enzyme with a lower catalytic efficiency. In some embodiments, the esterase is a newly engineered enzyme with a cholesterol esterase backbone. Such enzymes have lower efficiency than typical commercially available esterases permitting lower levels of esterase production in a system optimized for ethanol production.

As used herein, certain esterases are useful in reducing metal ion content in DCO. Exemplary esterases include lipases.

In certain embodiments, the method utilizes an esterase defined by EC 3.1.1.1 (a carboxylic-ester hydrolase) or EC 3.1.1.3 (a triacylglycerol lipase). A yeast or bacteria can be genetically modified to produce carboxylic-ester hydrolase or triacylglycerol lipase.

In certain embodiments, the method utilizes a CALB lipase. A yeast or bacteria can be genetically modified to produce CALB lipase. Unlike some general lipases, the CALB lipase, as well as some cholesterol esterases, favor the production of FAEE versus FFA production.

Fermentation in the presence of a microorganism that produces a low level of active CALB lipase reduces the metal concentration in DCO by at least about 20% to 90%, for example, by about 20%, 30%, 40%, 50%, 60%, 70%, 80%, or 90%. In some aspects, the metal concentration can be reduced to below 10 ppm.

The metal concentration of DCO can be further reduced through post processes such as water degumming as described in U.S. Patent Application 2019/0376002.

Fermentation conditions for commercial ethanol production are different from those conditions optimized to produce enzymes such as esterases. Typically, growth of an organism for the purpose of producing enzyme commercially focuses on conditions for producing a cleaner less variable enzyme stream as fast and high in enzyme quantity as possible. For example, conditions for growth of an enzyme-producing yeast include low solids content (6% or below) in the growth media, a mid-range pH 5-7 (depending on the organism), a temperature around 30° C., with excess nutrients, in an aerobic system. Yeasts grown for enzyme production are typically sensitivity to a high ethanol titer, so growth conditions are manipulated to minimize ethanol production.

In contrast, conditions for commercial ethanol production include longer fermentation times, for example, up to 90 hours, high solids content of the fermentation broth (between 20% and 50%), a pH of about 4.0 to 5.0, a temperature of about 30° C. to 35° C., e.g. about 32° C. to about 34° C., in an anaerobic system. Lipase producing microorganisms when present in a commercial ethanol fermentation are not in optimal enzyme producing conditions, and thus the amount of lipase is regulated such that the concentration is at a level sufficient to achieve decreased metal content of DCO, but not high enough to increase FFA and/or metal content of DCO.

Long-chain lipase units (LCLU) refers to the standard units for measuring lipase activity and are described in patent application, WO 2015181308 A1. Such units can be measured by detecting the hydrolysis product, p-nitrophenol (PNP), of PNP-palmitate and measuring its resulting absorbance at 405 nm. 1 unit is defined as the amount of enzyme to release 1 μmol of PNP per minute. However, as used herein, the amount of lipase produced during propagation and/or fermentation was based upon Lipase Unit (LU) equivalency, e.g. where the lipase produced is present in the fermentation in an amount equivalent to about 0.03 to about 0.70 LU/g dry solids (DS), or about 0.01 to about 1.00 LU/g dry solids; where the lipase produced is present in the fermentation in an amount from about 0.0006% to about 0.0150% w/w DS, or from about 0.0001% to about 0.030% w/w DS; where the lipase produced is present in the fermentation in an amount from about 0.02% to about 0.5% w/w corn oil, or from about 0.01% to about 1.0% w/w corn oil; or where the lipase produced is present in the fermentation in an amount from about 5 L to about 100 L in a 550,000 gal fermentation vat.

In some aspects, a lipase producing microorganism will generate about 0.15 to about 0.3 lipase units (LU) per gram of dry solids in the early stages of fermentation or during propagation in order to decrease metal content in the DCO.

In other aspects, the lipase produced by the esterase-producing microorganism is present in an amount sufficient to achieve decreased levels of FFA, for example, at least a 10% reduction in FFA levels, at least a 20% reduction in FFA levels, at least a 30% reduction in FFA levels, at least a 40% reduction in FFA levels, at least a 50% reduction in FFA levels, or at least a 75% reduction in FFA levels in crude DCO relative to a fermentation in the absence of an esterase-producing microorganism. In some aspects, the methods provided herein result in crude DCO having an FFA content of less than about 5%, about 4%, about 3%, about 2%, or about 1% by weight.

In other aspects, the lipase produced by the esterase-producing microorganism is present in an amount sufficient to achieve increased levels of FAEE, for example, at least a 10% increase in FAEE levels, at least a 20% increase in FAEE levels, at least a 30% increase in FAEE levels, at least a 40% increase in FAEE levels, at least a 50% increase in FAEE levels, or at least a 75% increase in FAEE levels in crude DCO relative to a fermentation in the absence of an esterase-producing microorganism. In some aspects, the methods provided herein result in crude DCO having an FAEE content of more than about 12%, about 15%, about 20%, about 25%, or about 30% by weight.

Likewise, the lipase produced by the esterase-producing microorganism is present in an amount sufficient to achieve decreased levels of metal, i.e. metal ion content, for example, at least about 10% to about 100% decrease in metal, i.e., at least about 20% to about 90%, at least about 30% to about 100%, at least about 40% to about 60%, at least about 50% to about 90%, etc., or at least about a 10% decrease in metal, at least about a 20% decrease in metal, at least about a 30% decrease in metal, at least about a 40% decrease in metal, at least about a 50% decrease in metal, at least about a 60% decrease in metal, at least about a 70% decrease in metal, at least about an 80% decrease in metal, or at least about a 90% decrease in metal in DCO relative to a DCO obtained from fermentation in the absence of an esterase-producing microorganism. While the decrease in metal, e.g. metal ions content, correlates with reduced FFA/increased FAEE, the correlation is not proportionate, and a small change in FFA/FAEE can substantially alter metal content in DCO.

In some aspects, the metals content in DCO produced according to the methods and compositions provided herein is less than about 10 ppm, or less than about 7 ppm, or less than about 5 ppm, or less than about 4 ppm, or 3 ppm, or 2 ppm, or 1 ppm.

In some embodiments, DCO is obtained by separating the corn oil from fermentation residue (e.g. stillage, thin stillage, or syrup) to provide an emulsion layer and a first aqueous layer. The corn oil is present in the emulsion layer and can be isolated from the emulsion by breaking the emulsion to provide a corn oil phase and an aqueous phase. The emulsion may be broken by addition of an emulsion breaking chemical such as a demulsifier or a polysorbate. The emulsion may be broken by adjusting the pH of the emulsion layer to a range of about pH 6.0 to 9.0, or about 7.0 to 8.0. Once the emulsion is broken, the corn oil phase is separated from the aqueous phase to provide the isolated DCO. Separating can be accomplished centrifugation or by simply allowing the phase separation to occur over time and decanting. In some aspects, the metals content in a renewable diesel feedstock extracted from a broken emulsion, i.e. the DCO obtained according to the methods and compositions provided herein, is reduced by at least about 50%, or by about 10% to about 90%, relative to the metals content in DCO obtained without the use of endogenous lipase. In some aspects, the metals content is less than about 10 ppm, or less than about 7 ppm, or less than about 5 ppm, or less than about 4 ppm, or 3 ppm, or 2 ppm, or 1 ppm. In some aspects, the FFA content in the produced DCO produced according to the methods and compositions provided herein is less than about 5%. In some aspects, the FAEE content in the DCO produced according to the methods and compositions provided herein is greater than about 12%, for example is greater than about 15%, about 20%, about 25%, or about 30%.

In some aspects, the lipase produced by the esterase-producing microorganism, or the lipase present in the ground corn, is present in the fermentation in an amount to achieve esterification of FFA; is present in the fermentation in an amount sufficient to achieve decreased FFA in DCO, for example, about 10% to about 50% less FFA relative to a fermentation in the absence of endogenous lipase; is present in the fermentation in an amount sufficient to achieve decreased metal content in the DCO, for example, at least about a 10% decrease in metal, at least about a 20% decrease in metal, at least about a 30% decrease in metal, at least about a 40% decrease in metal, or at least about a 50% decrease in metal, or more, relative to a fermentation in the absence of endogenous lipase.

In some aspects, the lipase produced in propagation or fermentation generates esters, determined by FAEE increase, and decreases FFA acid in the system. This shift correlates to the reduction in metals. In some aspects, the increase in FAEE is about 5% to about 30%, for example, about 15% to about 20%, and a decrease in FFA to about 5% to about 3%. In other words, the endogenous lipase effects an esterification of the FFA in the system as measured by the increase in FAEE content in the DCO.

Lipase activity in a given system can be measured by obtaining a ratio of FFA to FAEE at various timepoints during propagation or fermentation, relative to the ratio of FFA to FAEE at the start of the propagation or fermentation, or time zero.

Other assays used to measure endogenous lipase activity can be modified to suit the purposes herein and are known to those skilled in the art.

EXAMPLES

The following examples are provided for illustrative purposes only and are not intended to limit the scope of the invention.

Example 1

Fermenting in the presence of a lipase (AKA esterase, E.C. 3.1.1.3) decreases the level of FFA by esterifying the FFA with ethanol to form FAEE, Lipases similar to the Lipozyme CALB L lipase (Le, with high sequence identity) preferentially perform the reaction over hydrolysis and/or transesterification of triglycerides.

In the present example, lipase was added at the beginning of bench-scale fermentations at varying levels. After approximately 90 hours of fermentation to form a beer, an emulsion was isolated from the beer by centrifugation. The oil was solvent extracted from the emulsion using chloroform. The solvent was evaporated, and the corresponding FAEE content was determined by an in-house GC-FID method and the FFA was determined by a method similar to AOCS Ca 5a-40.

The resulting corn oil compositions exhibit dose dependent reduction in FFA content, which correlates to a reduced metal ion content.

TABLE 1

Lipozyme CALB L lipase enzyme approximate dosing and corresponding emulsion FAEE and FFA content.

| LU/g DS[a] | % w/w DS | % w/w Corn Oil | L/550,000 gal Ferm | % FAEE (% w/w)[b] | FFA (% w/w)[b] |
|---|---|---|---|---|---|
| 0 | 0% | 0% | 0 | 13.0% | 17.9% |
| 0.03 | 0.0006% | 0.02% | 5 | 18.6% | 14.1% |
| 0.06 | 0.0013% | 0.04% | 10 | 21.3% | 10.6% |
| 0.32 | 0.0065% | 0.20% | 50 | 29.3% | 4.3% |
| 0.65 | 0.0130% | 0.40% | 100 | 31.2% | 3.9% |

[a]Lipase Unit (LU), Dry Solids (DS) - 1 LU, quantity of enzyme to produce 1 μmol of butyric acid from tributyrin
[b]FFA and FAEE content of oil solvent extracted from the emulsion FFA content can be correlated to the metal soap content in (DCO). When breaking an oil water emulsion in a stillage stream by increasing the pH (e.g., with sodium hydroxide) to pH 7 or pH 8, one or more metal soaps can be formed. The increase in pH drives deprotonation of FFA forming a salt between fatty acid carboxylate with existing cationic metals ($Na^+$, $K^+$, $Mg^{2+}$, $Ca^{2+}$, etc.). Therefore, by reducing the level of FFA in the emulsion, the amount of metal soaps formed can also be reduced resulting in less carryover into the DCO during separation. In addition, the presence of FAEE can decrease the viscosity of the DCO improving corn oil extraction or additional separations carried out to further reduce DCO metal content.

Example 2

FFA and metals content were shown to decrease in DCO produced in plant scale fermentation with varying amounts of lipase added during fermentation. Lipase was added at the beginning of plant-scale fermentation, to reflect endogenously produced lipase, at varying levels. The oil was isolated at the plant by previously described methodologies. The FAEE and FFA content of the DCO was determined as previously described. Total phosphorous and metals (Ca, Cu, Fe, Mg, Mn, K, P, Na, S, and Zn) were determined by AOAC 2014.11.

The data in Table 2 shows FFA content of oil extracted from fermentation with or without lipase at varying levels. DCO FFA content can be determined by test method AOCS Ca 5a-40.

TABLE 2

Effect of Exogenous Lipase Enzyme Dosing on FFA and Total Phosphorus and Metals

| Lipase Dose (L/550,000 gal) | Lipase Name | Approximate Fermentation pH | Approximate Fermentation Hours | % FFA in Oil | Total Phosphorous and Metals PPM |
|---|---|---|---|---|---|
| 0 | NA | 4.3 | 80 | 7.3% | 276 |
| 5 | Lipozyme CALB L | 4.3 | 80 | 4.2% | 57 |
| 0 | NA | 4.6 | 90 | 4.8% | 224 |
| 3 | Lipozyme CALB L | 4.6 | 90 | 3.8% | 51 |

Example 3

A fermentation vat containing ground corn and water is inoculated with an ethanologen, S. cerevisiae, and a bacteria engineered to produce a lipase having the amino acid sequence of SEQ ID NO: 1. The yeast is added to the fermentation during the fermenter fill at a rate of 5 to 100 pounds of active dry yeast (ADY) per 100,000 gallons of fermentation mash. The bacteria are added to the fermentation for production of lipase in an amount sufficient to decrease metal ion content in the resulting DCO by at least about 20% relative to a fermentation carried out in the absence of a lipase producing bacteria. Fermentation proceeds over 74-88 hours, producing a commercially significant quantity of ethanol in that time.

DCO is obtained by separating the corn oil from fermentation residue to provide an emulsion layer and a first aqueous layer and breaking the emulsion layer by adjusting the pH to about pH 8 to provide a corn oil layer and a second aqueous layer. The corn oil layer is separated from the second aqueous layer to provide the isolated DCO composition. Separating can be accomplished by simply allowing the phase separation to occur over time and decanting or centrifuging to isolate the oil layer. Metal ion content in the produced DCO is assessed and found to be decreased by 20% relative to the control (DCO obtained from a similar fermentation in the absence of endogenous lipase).

Example 4

Yeast can be propagated, acclimated, and conditioned by incubating the yeast in a prefermenter or propagation tank. In this experiment, feedstock is inoculated with about 5 to 50 pounds of yeast per 10,000 gallon volume of fermenter volume in a prefermenter or propagation tank. The yeast is engineered to express lipase. Incubation proceeds over a time period of 16 hours during the propagation stage, which is aerated to encourage yeast growth. The prefermenter used to inoculate the main fermenter is about 10% by volume the capacity of the main fermenter. After propagation, the yeast cells are lysed, and the lysate is added to a fermentation tank along with a yeast ethanologen. Fermentation is carried out under conditions optimized for commercial ethanol production. After an 88 hour fermentation, ethanol is distilled from the beer and DCO is isolated from the stillage. Metal ion content in the DCO is assessed and found to be decreased by 80% relative to the control (DCO obtained from a similar fermentation in the absence of endogenous lipase).

Example 5

In this experiment, feedstock is inoculated with About 5 to 50 pounds of yeast per 10,000 gallon volume of fermenter volume in a prefermenter or propagation tank. The yeast is engineered to express lipase. Incubation proceeds over a time period of 12 hours during the propagation stage, which is aerated to encourage yeast growth and lipase production. The prefermenter used to inoculate the main fermenter is about 10% by volume the capacity of the main fermenter. After propagation, the yeast cells are added to a fermentation tank. Fermentation is carried out under conditions optimized for commercial ethanol production. After a 70 hour fermentation, ethanol is distilled from the beer and DCO is isolated from the stillage. Metal ion content in the DCO is assessed and found to be decreased by 50% relative to the control (DCO obtained from a similar fermentation in the absence of endogenous lipase).

Example 6

In this experiment, genetically modified ground corn engineered to produce lipase is inoculated with an ethanologen for commercial production of ethanol. The ethanologen is added to the fermentation during the fermenter fill at a rate of 100 pounds of active dry yeast (ADY) per 100,000 gallons of fermentation mash. Fermentation proceeds over 74-88 hours, producing a commercially significant quantity of ethanol in that time. After fermentation, ethanol is distilled from the beer and DCO is isolated from the stillage. Metal ion content in the isolated DCO is assessed and found to be decreased by 55% relative to the control (DCO obtained from a similar fermentation in the absence of endogenous lipase).

Example 7

In this experiment, ground corn is mixed with water and cooked to liquefy starch. The cooked slurry is transferred to a fermenter where it is mixed with yeast and lipase. Fermentation is carried out under conditions optimized for commercial ethanol production. After a 75 hour fermentation, ethanol is distilled from the beer and DCO is isolated from the stillage. Metal ion content in the DCO assessed and found to be decreased by 50% relative to the control (DCO obtained from a similar fermentation in the absence of endogenous lipase).

Further Examples

1. A method of producing distillers corn oil (DCO), the method comprising:
(a) inoculating a feedstock:
(i) with a combination of a first microorganism which is an ethanologen and a second microorganism for producing lipase;
(ii) with an ethanologen, wherein the ethanologen is a yeast genetically modified to produce lipase; or
(iii) with an ethanologen, wherein the feedstock contains starch from a genetically modified plant engineered to produce lipase; and (b) fermenting the feedstock to produce ethanol and DCO.

2. The method of example 1, wherein the step of (a)(i) includes inoculating a feedstock in a propagation tank or a fermentation tank with the ethanologen and the second microorganism.

3. The method of example 1, wherein the step of (a)(i) includes inoculating a feedstock in a first propagation tank with the ethanologen and inoculating a feedstock in a second propagation tank (side tank propagation) with the second microorganism, and wherein step (b) further comprises fermenting contents obtained from the first propagation tank with contents obtained from a second propagation tank in the presence of feedstock for ethanol production.

4. The method of example 1, wherein the step of (a)(i) includes inoculating a feedstock in a fermentation tank with the ethanologen and inoculating a feedstock in a propagation tank (side tank propagation) with the second microorganism, and wherein step (b) further comprises adding the contents obtained from the propagation tank to the fermentation tank and fermenting feedstock for ethanol production.

5. The method of example 1, wherein the DCO exhibits decreased levels of cationic metals ($Na^+$, $K^+$, $Mg^{2+}$, $Ca^{2+}$, etc.) or phosphorus relative to the levels of cationic metals or phosphorus present in DCO produced in the absence of a lipase-producing microorganism, yeast, or plant.

6. The method of example 1, wherein the DCO exhibits decreased soap content relative to the soap content in DCO produced in the absence of a lipase-producing microorganism, yeast, or plant.

7. The method of example 1, wherein the DCO exhibits decreased viscosity relative to the viscosity of a DCO produced in the absence of a lipase-producing microorganism, yeast, or plant.

8. The method of example 1, wherein the DCO comprises increased FAEE/decreased FFA relative to the FAEE/FFA content of a DCO produced in the absence of a lipase-producing microorganism, yeast, or plant.

9. The method of example 1, wherein the lipase produced is present in the fermentation in an amount equivalent to about 0.01 to about 1.00 LU/g dry solids (DS); about 0.0001% to about 0.0300% w/w DS; about 0.02% to about 0.5% w/w corn oil; or about 1 L to about 100 L in a 550,000 gal fermentation vat.

10. The method of example 1, wherein the lipase produced is present in an amount sufficient to reduce metal ion content or phosphorus content in DCO by at least about 20% relative to a fermentation in the absence of a lipase-producing microorganism, yeast, or plant.

11. The method of example 1, wherein the lipase produced is present in an amount sufficient to reduce metal ion content or phosphorus content in DCO by at least about 50% relative to a fermentation in the absence of a lipase-producing microorganism, yeast, or plant.

12. The method of example 1, wherein the lipase produced is present in the fermentation in an amount sufficient to reduce FFA content in DCO to less than about 15% w/w relative to a fermentation in the absence of a lipase-producing microorganism, yeast, or plant.

13. The method of example 1(a)(i), wherein the ethanologen is *S. cerevisiae* and the second microorganism is a genetically modified yeast engineered to produce lipase, and wherein the lipase produced by the second yeast is present in the fermentation in an amount sufficient to reduce metal ion content or phosphorus content in DCO by at least about 10% relative to a fermentation in the absence of a lipase-producing microorganism, yeast, or plant.

14. The method of example 1(a)(i), wherein the ethanologen is *S. cerevisiae* and the second microorganism is a bacteria engineered to produce lipase, and wherein the lipase produced by the bacteria is present in the fermentation in an amount sufficient to reduce metal ion content or phosphorus content in DCO by at least about 10% relative to a fermentation in the absence of a lipase-producing microorganism, yeast, or plant.

15. The method of example 1(a)(ii), wherein the yeast is *S. cerevisiae* and the lipase produced by the yeast is present in the fermentation in an amount equivalent to about 0.03 to about 0.70 LU/g dry solids (DS).

16. A composition comprising two microorganisms, wherein the first microorganism is an ethanologen which is a yeast strain and the second microorganism is a yeast strain or bacteria genetically modified to produce lipase under one or more conditions for ethanol production; wherein one or more conditions for ethanol production are selected from the group consisting of:
   (i) anaerobic fermentation;
   (ii) fermentation solids content of at least about 20%;
   (iii) a pH of about 4.0 to about 5.0; and
   (iv) a temperature of about 37° C.

17. The composition of example 16, wherein the ethanologen is *S. cerevisiae*.

18. The composition of example 16, wherein the second microorganism is a bacteria.

19. The composition of example 16, wherein the second microorganism is a yeast strain.

20. A fermenter comprising the composition of example 16, water, and feedstock.

21. A method of producing DCO as a by-product of fermentation associated with ethanol production, the method comprising: (a) inoculating a feedstock with a combination of two yeast strains, wherein the first yeast strain is an ethanologen and the second yeast strain produces lipase; and (b) fermenting the feedstock to produce ethanol and DCO, wherein the metal ion content or phosphorus content in the emulsion is decreased by at least about 10% relative to a DCO obtained as the by-product of fermentation in the absence of a lipase producing yeast.

22. The method of example 21, wherein the ethanol titer after fermentation is unchanged relative to the same fermentation performed in the absence of the lipase expressing yeast strain.

23. A method of producing DCO, comprising:
providing a first composition comprising water and ground corn;
inoculating the first composition with: (i) a combination of an ethanologen, which is a first yeast for fermentation of the ground corn, and a second yeast engineered to produce lipase; or (ii) an ethanologen which is genetically modified to produce lipase; fermenting the composition under conditions to form a second composition comprising DCO, wherein the lipase produced is sufficient to reduce metal ion content or phosphorus content in the resulting DCO.

24. A method of producing DCO, comprising:
providing a first composition comprising water and ground corn, wherein the ground corn comprises lipase, or is sourced from GMO corn expressing lipase;
inoculating the first composition with yeast; and
fermenting the first composition under conditions to form a second composition comprising DCO.

25. The method of example 23 or example 24, further comprising isolating an emulsion comprising DCO; breaking the emulsion comprising the DCO; and isolating the DCO to obtain a renewable diesel feedstock containing less than about 10 ppm metal ions.

26. A composition for ethanol production comprising ground corn, water, and *S. cerevisiae*, wherein the *S. cerevisiae* is genetically modified to produce lipase, and wherein the ground corn is present in the composition in an amount of about 20% to 50% by weight solids.

27. The composition of example 26, wherein the *S. cerevisiae* comprises a nucleotide sequence encoding a polypeptide selected from the group consisting of SEQ ID NOs: 1-27.

28. The composition of example 26, wherein the lipase is produced in an amount sufficient to reduce metal ion content or phosphorus content in DCO.

29. A composition for ethanol production comprising ground corn, water, and *S. cerevisiae*, wherein the ground corn comprises lipase in an amount sufficient to reduce metal ion content or phosphorus content in distillers corn oil.

30. The composition of example 29, wherein the ground corn is genetically modified to express lipase.

31. A method of producing DCO, comprising fermenting feedstock in presence of an esterase or lipase, wherein the DCO exhibits at least about a 10% to about 100% reduction in metal ion content or phosphorus content relative to a DCO produced in the absence of an esterase or lipase.

32. The method of example 31, wherein the esterase or lipase is present in an amount sufficient to reduce metal ion content or phosphorus content in DCO by at least about 50% relative to a fermentation in the absence of esterase or lipase.

33. The method of example 31, wherein the esterase or lipase is present in an amount sufficient to reduce metal ion content or phosphorus content in DCO by at least about 80% relative to a fermentation in the absence of esterase or lipase.

34. The method of example 31, wherein the metal ion is selected from the group consisting of $Na^+$, $K^+$, $Mg^{2+}$, and $Ca^{2+}$.

35. The method of example 31, wherein the phosphorus content is reduced.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. A method of producing DCO, comprising fermenting a ground, grain-based feedstock comprising ground corn in presence of an active lipase, wherein the DCO produced exhibits at least about a 10% to about 100% reduction in metal ion content or phosphorus content relative to a DCO produced in the absence of the active lipase.

2. The method of claim 1, wherein the metal ion is selected from the group consisting of $Na^+$, $K^+$, $Mg^{2+}$, and $Ca^{2+}$.

3. The method of claim 1, wherein the phosphorus content is reduced.

4. The method of claim 1, further comprising isolating an emulsion comprising DCO; breaking the emulsion comprising the DCO; and isolating the DCO to obtain a renewable diesel feedstock containing less than about 10 ppm metal ions.

5. The method of claim 1, wherein the active lipase is a triacylglycerol lipase.

6. The method of claim 1, wherein the DCO produced exhibits at least about a 50% reduction in metal ion content or phosphorus content relative to a DCO produced in the absence of the active lipase.

7. The method of claim 1, wherein the DCO produced exhibits at least about an 80% reduction in metal ion content or phosphorus content relative to a DCO produced in the absence of the active lipase.

* * * * *

SEQUENCE LISTING

```
<160> NUMBER OF SEQ ID NOS: 27

<210> SEQ ID NO 1
<211> LENGTH: 327
<212> TYPE: PRT
<213> ORGANISM: Artificial Sequence
<220> FEATURE:
```

<223> OTHER INFORMATION: Synthetic

<400> SEQUENCE: 1

Met Ala Leu Pro Ser Gly Ser Asp Pro Ala Phe Ser Gln Pro Lys Ser
1               5                   10                  15

Val Leu Asp Ala Gly Leu Thr Cys Gln Gly Ala Ser Pro Ser Ser Val
            20                  25                  30

Ser Lys Pro Ile Leu Leu Val Pro Gly Thr Gly Thr Thr Gly Pro Gln
        35                  40                  45

Ser Phe Asp Ser Asn Trp Ile Pro Leu Ser Thr Gln Leu Gly Tyr Thr
    50                  55                  60

Pro Cys Trp Ile Ser Pro Pro Phe Met Leu Asn Asp Thr Gln Val
65                  70                  75                  80

Asn Thr Glu Tyr Met Val Asn Ala Ile Thr Ala Leu Tyr Ala Gly Ser
                85                  90                  95

Gly Asn Asn Lys Leu Pro Val Leu Thr Trp Ser Gln Gly Gly Leu Val
            100                 105                 110

Ala Gln Trp Gly Leu Thr Phe Phe Pro Ser Ile Arg Ser Lys Val Asp
        115                 120                 125

Arg Leu Met Ala Phe Ala Pro Asp Tyr Lys Gly Thr Val Leu Ala Gly
    130                 135                 140

Pro Leu Asp Ala Leu Ala Val Ser Ala Pro Ser Val Trp Gln Gln Thr
145                 150                 155                 160

Thr Gly Ser Ala Leu Thr Thr Ala Leu Arg Asn Ala Gly Gly Leu Thr
                165                 170                 175

Gln Ile Val Pro Thr Thr Asn Leu Tyr Ser Ala Thr Asp Glu Ile Val
            180                 185                 190

Gln Pro Gln Val Ser Asn Ser Pro Leu Asp Ser Ser Tyr Leu Phe Asn
        195                 200                 205

Gly Lys Asn Val Gln Ala Gln Ala Val Cys Gly Pro Leu Phe Val Ile
    210                 215                 220

Asp His Ala Gly Ser Leu Thr Ser Gln Phe Ser Tyr Val Val Gly Arg
225                 230                 235                 240

Ser Ala Leu Arg Ser Thr Thr Gly Gln Ala Arg Ser Ala Asp Tyr Gly
                245                 250                 255

Ile Thr Asp Cys Asn Pro Leu Pro Ala Asn Asp Leu Thr Pro Glu Gln
            260                 265                 270

Lys Val Ala Ala Ala Leu Leu Ala Pro Ala Ala Ala Ile Val
        275                 280                 285

Ala Gly Pro Lys Gln Asn Cys Glu Pro Asp Leu Met Pro Tyr Ala Arg
    290                 295                 300

Pro Phe Ala Val Gly Lys Arg Thr Cys Ser Gly Ile Val Thr Pro Leu
305                 310                 315                 320

Glu His His His His His His
                325

<210> SEQ ID NO 2
<211> LENGTH: 342
<212> TYPE: PRT
<213> ORGANISM: Artificial Sequence
<220> FEATURE:
<223> OTHER INFORMATION: Synthetic

<400> SEQUENCE: 2

Met Lys Leu Leu Ser Leu Thr Gly Val Ala Gly Val Leu Ala Thr Cys
1               5                   10                  15

Val Ala Ala Thr Pro Leu Val Lys Arg Leu Pro Ser Gly Ser Asp Pro
            20                  25                  30

Ala Phe Ser Gln Pro Lys Ser Val Leu Asp Ala Gly Leu Thr Cys Gln
                35                  40                  45

Gly Ala Ser Pro Ser Ser Val Ser Lys Pro Ile Leu Leu Val Pro Gly
    50                  55                  60

Thr Gly Thr Thr Gly Pro Gln Ser Phe Asp Ser Asn Trp Ile Pro Leu
65                  70                  75                  80

Ser Thr Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
            100                 105                 110

Thr Ala Leu Tyr Ala Gly Ser Gly Asn Asn Lys Leu Pro Val Leu Thr
        115                 120                 125

Trp Ser Gln Gly Gly Leu Val Ala Gln Trp Gly Leu Thr Phe Phe Pro
    130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175

Pro Ser Val Trp Gln Gln Thr Thr Gly Ser Ala Leu Thr Thr Ala Leu
            180                 185                 190

Arg Asn Ala Gly Gly Leu Thr Gln Ile Val Pro Thr Thr Asn Leu Tyr
        195                 200                 205

Ser Ala Thr Asp Glu Ile Val Gln Pro Gln Val Ser Asn Ser Pro Leu
    210                 215                 220

Asp Ser Ser Tyr Leu Phe Asn Gly Lys Asn Val Gln Ala Gln Ala Val
225                 230                 235                 240

Cys Gly Pro Leu Phe Val Ile Asp His Ala Gly Ser Leu Thr Ser Gln
                245                 250                 255

Phe Ser Tyr Val Val Gly Arg Ser Ala Leu Arg Ser Thr Thr Gly Gln
            260                 265                 270

Ala Arg Ser Ala Asp Tyr Gly Ile Thr Asp Cys Asn Pro Leu Pro Ala
        275                 280                 285

Asn Asp Leu Thr Pro Glu Gln Lys Val Ala Ala Ala Leu Leu Ala
    290                 295                 300

Pro Ala Ala Ala Ile Val Ala Gly Pro Lys Gln Asn Cys Glu Pro
305                 310                 315                 320

Asp Leu Met Pro Tyr Ala Arg Pro Phe Ala Val Gly Lys Arg Thr Cys
                325                 330                 335

Ser Gly Ile Val Thr Pro
            340

<210> SEQ ID NO 3
<211> LENGTH: 339
<212> TYPE: PRT
<213> ORGANISM: Artificial Sequence
<220> FEATURE:
<223> OTHER INFORMATION: Synthetic

<400> SEQUENCE: 3

Met Lys Tyr Leu Leu Pro Thr Ala Ala Ala Gly Leu Leu Leu Leu Ala
1               5                   10                  15

Ala Gln Pro Ala Met Ala Leu Pro Ser Gly Ser Asp Pro Ala Phe Ser
            20                  25                  30

Gln Pro Lys Ser Val Leu Asp Ala Gly Leu Thr Cys Gln Gly Ala Ser
                35                  40                  45

Pro Ser Ser Val Ser Lys Pro Ile Leu Leu Val Pro Gly Thr Gly Thr
 50                  55                  60

Thr Gly Pro Gln Ser Phe Asp Ser Asn Trp Ile Pro Leu Ser Thr Gln
 65                  70                  75                  80

Leu Gly Tyr Thr Pro Cys Trp Ile Ser Pro Pro Phe Met Leu Asn
                85                  90                  95

Asp Thr Gln Val Asn Thr Glu Tyr Met Val Asn Ala Ile Thr Ala Leu
                100                 105                 110

Tyr Ala Gly Ser Gly Asn Asn Lys Leu Pro Val Leu Thr Trp Ser Gln
                115                 120                 125

Gly Gly Leu Val Ala Gln Trp Gly Leu Thr Phe Phe Pro Ser Ile Arg
 130                 135                 140

Ser Lys Val Asp Arg Leu Met Ala Phe Ala Pro Asp Tyr Lys Gly Thr
145                 150                 155                 160

Val Leu Ala Gly Pro Leu Asp Ala Leu Ala Val Ser Ala Pro Ser Val
                165                 170                 175

Trp Gln Gln Thr Thr Gly Ser Ala Leu Thr Thr Ala Leu Arg Asn Ala
                180                 185                 190

Gly Gly Leu Thr Gln Ile Val Pro Thr Thr Asn Leu Tyr Ser Ala Thr
                195                 200                 205

Asp Glu Ile Val Gln Pro Gln Val Ser Asn Ser Pro Leu Asp Ser Ser
                210                 215                 220

Tyr Leu Phe Asn Gly Lys Asn Val Gln Ala Gln Ala Val Cys Gly Pro
225                 230                 235                 240

Leu Phe Val Ile Asp His Ala Gly Ser Leu Thr Ser Gln Phe Ser Tyr
                245                 250                 255

Val Val Gly Arg Ser Ala Leu Arg Ser Thr Thr Gly Gln Ala Arg Ser
                260                 265                 270

Ala Asp Tyr Gly Ile Thr Asp Cys Asn Pro Leu Pro Ala Asn Asp Leu
                275                 280                 285

Thr Pro Glu Gln Lys Val Ala Ala Ala Leu Leu Ala Pro Ala Ala
                290                 295                 300

Ala Ala Ile Val Ala Gly Pro Lys Gln Asn Cys Glu Pro Asp Leu Met
305                 310                 315                 320

Pro Tyr Ala Arg Pro Phe Ala Val Gly Lys Arg Thr Cys Ser Gly Ile
                325                 330                 335

Val Thr Pro

<210> SEQ ID NO 4
<211> LENGTH: 326
<212> TYPE: PRT
<213> ORGANISM: Artificial Sequence
<220> FEATURE:
<223> OTHER INFORMATION: Synthetic

<400> SEQUENCE: 4

Ala Leu Pro Ser Gly Ser Asp Pro Ala Phe Ser Gln Pro Lys Ser Val
 1               5                  10                  15

Leu Asp Ala Gly Leu Thr Cys Gln Gly Ala Ser Pro Ser Ser Val Ser
                20                  25                  30

Lys Pro Ile Leu Leu Val Pro Gly Thr Gly Thr Thr Gly Pro Gln Ser
                35                  40                  45

```
Phe Asp Ser Asn Trp Ile Pro Leu Ser Thr Gln Leu Gly Tyr Thr Pro
 50                  55                  60

Cys Trp Ile Ser Pro Pro Phe Met Leu Asn Asp Thr Gln Val Asn
 65                  70                  75                  80

Thr Glu Tyr Met Val Asn Ala Ile Thr Ala Leu Tyr Ala Gly Ser Gly
                 85                  90                  95

Asn Asn Lys Leu Pro Val Leu Thr Trp Ser Gln Gly Gly Leu Val Ala
                100                 105                 110

Gln Trp Gly Leu Thr Phe Phe Pro Ser Ile Arg Ser Lys Val Asp Arg
                115                 120                 125

Leu Met Ala Phe Ala Pro Asp Tyr Lys Gly Thr Val Leu Ala Gly Pro
145                 150                 155                 160

Leu Asp Ala Leu Ala Val Ser Ala Pro Ser Val Trp Gln Gln Thr Thr
145                 150                 155                 160

Gly Ser Ala Leu Thr Thr Ala Leu Arg Asn Ala Gly Gly Leu Thr Gln
                165                 170                 175

Ile Val Pro Thr Thr Asn Leu Tyr Ser Ala Thr Asp Glu Ile Val Gln
                180                 185                 190

Pro Gln Val Ser Asn Ser Pro Leu Asp Ser Ser Tyr Leu Phe Asn Gly
                195                 200                 205

Lys Asn Val Gln Ala Gln Ala Val Cys Gly Pro Leu Phe Val Ile Asp
                210                 215                 220

His Ala Gly Ser Leu Thr Ser Gln Phe Ser Tyr Val Val Gly Arg Ser
225                 230                 235                 240

Ala Leu Arg Ser Thr Thr Gly Gln Ala Arg Ser Ala Asp Tyr Gly Ile
                245                 250                 255

Thr Asp Cys Asn Pro Leu Pro Ala Asn Asp Leu Thr Pro Glu Gln Lys
                260                 265                 270

Val Ala Ala Ala Leu Met Ala Pro Ala Ala Ala Ile Val Ala
                275                 280                 285

Gly Pro Lys Gln Asn Cys Glu Pro Asp Leu Met Pro Tyr Ala Arg Pro
                290                 295                 300

Phe Ala Val Gly Lys Arg Thr Cys Ser Gly Ile Val Thr Pro Leu Glu
305                 310                 315                 320

His His His His His His
                325

<210> SEQ ID NO 5
<211> LENGTH: 328
<212> TYPE: PRT
<213> ORGANISM: Artificial Sequence
<220> FEATURE:
<223> OTHER INFORMATION: Synthetic

<400> SEQUENCE: 5

Met Ala Asp Asp Asp Asp Leu Pro Ser Gly Ser Asp Pro Ala Phe
 1               5                  10                  15

Ser Gln Pro Lys Ser Val Leu Asp Ala Gly Leu Thr Cys Gln Gly Ala
                 20                  25                  30

Ser Pro Ser Ser Val Ser Lys Pro Ile Leu Leu Val Pro Gly Thr Gly
                 35                  40                  45

Thr Thr Gly Pro Gln Ser Phe Asp Ser Asn Trp Ile Pro Leu Ser Thr
                 50                  55                  60

Gln Leu Gly Tyr Thr Pro Cys Trp Ile Ser Pro Pro Pro Phe Met Leu
 65                  70                  75                  80
```

Asn Asp Thr Gln Val Asn Thr Glu Tyr Met Val Asn Ala Ile Thr Ala
                85                  90                  95

Leu Tyr Ala Gly Ser Gly Asn Asn Lys Leu Pro Val Leu Thr Trp Ser
            100                 105                 110

Gln Gly Gly Leu Val Ala Gln Trp Gly Leu Thr Phe Phe Pro Ser Ile
        115                 120                 125

Arg Ser Lys Val Asp Arg Leu Met Ala Phe Ala Pro Asp Tyr Lys Gly
    130                 135                 140

Thr Val Leu Ala Gly Pro Leu Asp Ala Leu Ala Val Ser Ala Pro Ser
145                 150                 155                 160

Val Trp Gln Gln Thr Thr Gly Ser Ala Leu Thr Thr Ala Leu Arg Asn
                165                 170                 175

Ala Gly Gly Leu Thr Gln Ile Val Pro Thr Thr Asn Leu Tyr Ser Ala
            180                 185                 190

Thr Asp Glu Ile Val Gln Pro Gln Val Ser Asn Ser Pro Leu Asp Ser
        195                 200                 205

Ser Tyr Leu Phe Asn Gly Lys Asn Val Gln Ala Gln Ala Val Cys Gly
    210                 215                 220

Pro Leu Phe Val Ile Asp His Ala Gly Ser Leu Thr Ser Gln Phe Ser
225                 230                 235                 240

Tyr Val Val Gly Arg Ser Ala Leu Arg Ser Thr Thr Gly Gln Ala Arg
                245                 250                 255

Ser Ala Asp Tyr Gly Ile Thr Asp Cys Asn Pro Leu Pro Ala Asn Asp
            260                 265                 270

Leu Thr Pro Glu Gln Lys Val Ala Ala Ala Leu Leu Ala Pro Ala
        275                 280                 285

Ala Ala Ala Ile Val Ala Gly Pro Lys Gln Asn Cys Glu Pro Asp Leu
    290                 295                 300

Met Pro Tyr Ala Arg Pro Phe Ala Val Gly Lys Arg Thr Cys Ser Gly
305                 310                 315                 320

Ile Val Thr Pro Ile Glu Gly Arg
                325

<210> SEQ ID NO 6
<211> LENGTH: 342
<212> TYPE: PRT
<213> ORGANISM: Artificial Sequence
<220> FEATURE:
<223> OTHER INFORMATION: Synthetic

<400> SEQUENCE: 6

Met Lys Leu Leu Ser Leu Thr Gly Val Ala Gly Val Leu Ala Thr Cys
1               5                   10                  15

Val Ala Thr Pro Leu Val Lys Arg Leu Pro Ser Gly Ser Asp Pro
            20                  25                  30

Ala Phe Ser Gln Pro Lys Ser Val Leu Asp Ala Gly Leu Thr Cys Gln
        35                  40                  45

Gly Ala Ser Pro Ser Ser Val Ser Lys Pro Ile Leu Leu Val Pro Gly
    50                  55                  60

Thr Gly Thr Thr Gly Pro Gln Ser Phe Asp Ser Asn Trp Ile Pro Leu
65                  70                  75                  80

Ser Ala Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
            100                 105                 110

```
Thr Ala Leu Tyr Ala Gly Ser Gly Asn Asn Lys Leu Pro Val Leu Thr
            115                 120                 125

Trp Ser Gln Gly Gly Leu Val Ala Gln Trp Gly Leu Thr Phe Phe Pro
130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175

Pro Ser Val Trp Gln Gln Thr Thr Gly Ser Ala Leu Thr Ala Leu
                180                 185                 190

Arg Asn Ala Gly Gly Leu Thr Gln Ile Val Pro Thr Thr Asn Leu Tyr
            195                 200                 205

Ser Ala Thr Asp Glu Ile Val Gln Pro Gln Val Ser Asn Ser Pro Leu
210                 215                 220

Asp Ser Ser Tyr Leu Phe Asn Gly Lys Asn Val Gln Ala Gln Ala Val
225                 230                 235                 240

Cys Gly Pro Leu Phe Val Ile Asp His Ala Gly Ser Leu Thr Ser Gln
                245                 250                 255

Phe Ser Tyr Val Val Gly Arg Ser Ala Leu Arg Ser Thr Thr Gly Gln
                260                 265                 270

Ala Arg Ser Ala Asp Tyr Gly Ile Thr Asp Cys Asn Pro Leu Pro Ala
            275                 280                 285

Asn Asp Leu Thr Pro Glu Gln Lys Val Ala Ala Ala Leu Leu Ala
            290                 295                 300

Pro Ala Ala Ala Ile Val Ala Gly Pro Lys Gln Asn Cys Glu Pro
305                 310                 315                 320

Asp Leu Met Pro Tyr Ala Arg Pro Phe Ala Val Gly Lys Arg Thr Cys
                325                 330                 335

Ser Gly Ile Val Thr Pro
            340

<210> SEQ ID NO 7
<211> LENGTH: 342
<212> TYPE: PRT
<213> ORGANISM: Artificial Sequence
<220> FEATURE:
<223> OTHER INFORMATION: Synthetic

<400> SEQUENCE: 7

Met Lys Leu Leu Ser Leu Thr Gly Val Ala Gly Val Leu Ala Thr Cys
1               5                   10                  15

Val Ala Ala Thr Pro Leu Val Lys Arg Leu Pro Ser Gly Ser Asp Pro
                20                  25                  30

Ala Phe Ser Gln Pro Lys Ser Val Leu Asp Ala Gly Leu Thr Cys Gln
            35                  40                  45

Gly Ala Ser Pro Ser Ser Val Ser Lys Pro Ile Leu Leu Val Pro Gly
    50                  55                  60

Thr Gly Thr Thr Gly Pro Gln Ser Phe Asp Ser Asn Trp Ile Pro Leu
65                  70                  75                  80

Ser Thr Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
                100                 105                 110

Thr Thr Leu Tyr Ala Gly Ser Gly Asn Asn Lys Leu Pro Val Leu Thr
            115                 120                 125
```

Trp Ser Gln Gly Gly Leu Val Ala Gln Trp Gly Leu Thr Phe Phe Pro
            130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175

Pro Ser Val Trp Gln Gln Thr Thr Gly Ser Ala Leu Thr Thr Ala Leu
            180                 185                 190

Arg Asn Ser Gly Gly Leu Thr Gln Ile Val Pro Thr Thr Asn Leu Tyr
            195                 200                 205

Ser Ala Thr Asp Glu Ile Val Gln Pro Gln Val Ser Asn Ser Pro Leu
210                 215                 220

Asp Ser Ser Tyr Leu Phe Asn Gly Lys Asn Val Gln Ala Gln Ala Val
225                 230                 235                 240

Cys Gly Pro Leu Phe Val Ile Asp His Ala Gly Ser Leu Thr Ser Gln
                245                 250                 255

Phe Ser Tyr Val Val Gly Arg Ser Ala Leu Arg Ser Thr Thr Gly Gln
            260                 265                 270

Ala Arg Ser Ala Asp Tyr Gly Ile Thr Asp Cys Asn Pro Leu Pro Ala
            275                 280                 285

Asn Asp Leu Thr Pro Glu Gln Lys Val Ala Ala Ala Leu Leu Ala
            290                 295                 300

Pro Ala Ala Ala Ile Val Ala Gly Pro Lys Gln Asn Cys Glu Pro
305                 310                 315                 320

Asp Leu Met Pro Tyr Ala Arg Pro Phe Ala Val Gly Lys Arg Thr Cys
                325                 330                 335

Ser Gly Ile Val Thr Pro
            340

<210> SEQ ID NO 8
<211> LENGTH: 326
<212> TYPE: PRT
<213> ORGANISM: Artificial Sequence
<220> FEATURE:
<223> OTHER INFORMATION: Synthetic

<400> SEQUENCE: 8

Ala Leu Pro Ser Gly Ser Asp Pro Ala Phe Ser Gln Pro Lys Ser Val
1               5                   10                  15

Leu Asp Ala Gly Leu Thr Cys Gln Gly Ala Ser Pro Ser Ser Val Ser
            20                  25                  30

Lys Pro Ile Leu Leu Val Pro Gly Thr Gly Thr Gly Pro Gln Ser
            35                  40                  45

Phe Asp Ser Asn Trp Ile Pro Leu Ser Thr Gln Leu Gly Tyr Thr Pro
50                  55                  60

Cys Trp Ile Ser Pro Pro Pro Phe Met Leu Asn Asp Thr Gln Val Asn
65                  70                  75                  80

Thr Glu Tyr Met Val Asn Ala Ile Thr Ala Leu Tyr Ala Gly Ser Gly
                85                  90                  95

Asn Asn Lys Leu Pro Val Leu Thr Trp Ser Gln Gly Gly Leu Val Ala
            100                 105                 110

Gln Trp Gly Leu Thr Phe Phe Pro Ser Ile Arg Ser Lys Val Asp Arg
            115                 120                 125

Leu Met Ala Phe Ala Pro Asp Tyr Lys Gly Thr Val Leu Ala Gly Pro
            130                 135                 140

-continued

```
Leu Asp Ala Leu Ala Val Ser Ala Pro Ser Val Trp Gln Gln Thr Thr
145                 150                 155                 160

Gly Ser Ala Leu Thr Thr Ala Leu Arg Asn Ala Gly Gly Leu Thr Gln
            165                 170                 175

Ile Val Pro Thr Thr Asn Leu Tyr Ser Ala Thr Asp Glu Ile Val Gln
            180                 185                 190

Pro Gln Val Ser Asn Ser Pro Leu Asp Ser Ser Tyr Leu Phe Asn Gly
        195                 200                 205

Lys Asn Val Gln Ala Gln Ala Val Cys Gly Pro Leu Phe Val Ile Gly
210                 215                 220

His Ala Gly Ser Leu Thr Ser Gln Phe Ser Tyr Val Val Gly Arg Ser
225                 230                 235                 240

Ala Leu Arg Ser Thr Thr Gly Gln Ala Arg Ser Ala Asp Tyr Gly Ile
            245                 250                 255

Thr Asp Cys Asn Pro Leu Pro Ala Asn Asp Leu Thr Pro Glu Gln Lys
            260                 265                 270

Val Ala Ala Ala Ala Leu Leu Ala Pro Ala Ala Ala Ile Val Ala
            275                 280                 285

Gly Pro Lys Gln Asn Cys Glu Pro Asp Leu Met Pro Tyr Ala Arg Pro
290                 295                 300

Phe Ala Val Gly Lys Arg Thr Cys Ser Gly Ile Val Thr Pro Leu Glu
305                 310                 315                 320

His His His His His His
            325
```

```
<210> SEQ ID NO 9
<211> LENGTH: 342
<212> TYPE: PRT
<213> ORGANISM: Artificial Sequence
<220> FEATURE:
<223> OTHER INFORMATION: Synthetic

<400> SEQUENCE: 9

Met Lys Leu Leu Ser Leu Thr Gly Val Ala Gly Val Leu Ala Thr Cys
1               5                   10                  15

Val Ala Ala Thr Pro Leu Val Lys Arg Leu Pro Ser Gly Ser Asp Pro
            20                  25                  30

Ala Phe Ser Gln Pro Lys Ser Val Leu Asp Ala Gly Leu Thr Cys Gln
        35                  40                  45

Gly Ala Ser Pro Ser Ser Val Ser Lys Pro Ile Leu Leu Val Pro Gly
    50                  55                  60

Thr Gly Thr Thr Gly Pro Gln Ser Phe Asp Ser Asn Trp Ile Pro Leu
65                  70                  75                  80

Ser Ala Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
            100                 105                 110

Thr Thr Leu Tyr Ala Gly Ser Gly Asn Asn Lys Leu Pro Val Leu Thr
        115                 120                 125

Trp Ser Gln Gly Gly Leu Val Ala Gln Trp Gly Leu Thr Phe Phe Pro
    130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175
```

```
Pro Ser Val Trp Gln Gln Thr Thr Gly Ser Ala Leu Thr Thr Ala Leu
                180                 185                 190

Arg Asn Ala Gly Gly Leu Thr Gln Ile Val Pro Thr Thr Asn Leu Tyr
            195                 200                 205

Ser Ala Thr Asp Glu Ile Val Gln Pro Gln Val Ser Asn Ser Pro Leu
        210                 215                 220

Asp Ser Ser Tyr Leu Phe Asn Gly Lys Asn Val Gln Ala Gln Ala Val
225                 230                 235                 240

Cys Gly Pro Leu Phe Val Ile Asp His Ala Gly Ser Leu Thr Ser Gln
                245                 250                 255

Phe Ser Tyr Val Val Gly Arg Ser Ala Leu Arg Ser Thr Thr Gly Gln
            260                 265                 270

Ala Arg Ser Ala Asp Tyr Gly Ile Thr Asp Cys Asn Pro Leu Pro Ala
        275                 280                 285

Asn Asp Leu Thr Pro Glu Gln Lys Val Ala Ala Ala Leu Leu Ala
290                 295                 300

Pro Ala Ala Ala Ile Val Ala Gly Pro Lys Gln Asn Cys Glu Pro
305                 310                 315                 320

Asp Leu Met Pro Tyr Ala Arg Pro Phe Ala Val Gly Lys Arg Thr Cys
                325                 330                 335

Ser Gly Ile Val Thr Pro
                340

<210> SEQ ID NO 10
<211> LENGTH: 325
<212> TYPE: PRT
<213> ORGANISM: Artificial Sequence
<220> FEATURE:
<223> OTHER INFORMATION: Synthetic

<400> SEQUENCE: 10

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
        35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Ala Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190
```

```
Gln Val Ser Asn Ser Pro Leu Asp Ser Ser Tyr Leu Phe Asn Gly Lys
            195                 200                 205

Asn Val Gln Ala Gln Ala Val Cys Gly Pro Leu Phe Val Ile Gly His
        210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Met Ala Pro Ala Ala Ala Ile Val Ala Gly
        275                 280                 285

Pro Lys Gln Asn Cys Glu Pro Asp Leu Met Pro Tyr Ala Arg Pro Phe
290                 295                 300

Ala Val Gly Lys Arg Thr Cys Ser Gly Ile Val Thr Pro Leu Glu His
305                 310                 315                 320

His His His His His
            325

<210> SEQ ID NO 11
<211> LENGTH: 321
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (313)..(313)
<223> OTHER INFORMATION: Xaa can be any naturally occurring amino acid

<400> SEQUENCE: 11

Met Ala Leu Pro Ser Gly Ser Asp Pro Ala Phe Ser Gln Pro Lys Ser
1               5                   10                  15

Val Leu Asp Ala Gly Leu Thr Cys Gln Gly Ala Ser Pro Ser Ser Val
            20                  25                  30

Ser Lys Pro Ile Leu Leu Val Pro Gly Thr Gly Thr Gly Pro Gln
        35                  40                  45

Ser Phe Asp Ser Asn Trp Ile Pro Leu Ser Thr Gln Leu Gly Tyr Thr
50                  55                  60

Pro Cys Trp Ile Ser Pro Pro Phe Met Leu Asn Asp Thr Gln Val
65                  70                  75                  80

Asn Thr Glu Tyr Met Val Asn Ala Ile Thr Ala Leu Tyr Ala Gly Ser
                85                  90                  95

Gly Asn Asn Lys Leu Pro Val Leu Thr Trp Ser Gln Gly Gly Leu Val
            100                 105                 110

Ala Gln Trp Gly Leu Thr Phe Phe Pro Ser Ile Arg Ser Lys Val Asp
        115                 120                 125

Arg Leu Met Ala Phe Ala Pro Asp Tyr Lys Gly Thr Val Leu Ala Gly
130                 135                 140

Pro Leu Asp Ala Leu Ala Val Ser Ala Pro Ser Val Trp Gln Gln Thr
145                 150                 155                 160

Thr Gly Ser Ala Leu Thr Thr Ala Leu Arg Asn Ala Gly Gly Leu Thr
                165                 170                 175

Gln Ile Val Pro Thr Thr Asn Leu Tyr Ser Ala Thr Asp Glu Ile Val
            180                 185                 190

Gln Pro Gln Val Ser Asn Ser Pro Leu Asp Ser Ser Tyr Leu Phe Asn
        195                 200                 205
```

Gly Lys Asn Val Gln Ala Gln Ala Val Cys Gly Pro Leu Phe Val Ile
210                 215                 220

Asp His Ala Gly Ser Leu Thr Ser Gln Phe Ser Tyr Val Val Gly Arg
225                 230                 235                 240

Ser Ala Leu Arg Ser Thr Thr Gly Gln Ala Arg Ser Ala Asp Tyr Gly
            245                 250                 255

Ile Thr Asp Cys Asn Pro Leu Pro Ala Asn Asp Leu Thr Pro Glu Gln
            260                 265                 270

Lys Val Ala Ala Ala Leu Leu Ala Pro Ala Ala Ala Ile Val
        275                 280                 285

Ala Gly Pro Lys Gln Asn Cys Glu Pro Asp Leu Met Pro Tyr Ala Arg
290                 295                 300

Pro Phe Ala Val Gly Lys Arg Thr Xaa Ser Gly Ile Val Thr Pro Ser
305                 310                 315                 320

Leu

<210> SEQ ID NO 12
<211> LENGTH: 321
<212> TYPE: PRT
<213> ORGANISM: Artificial Sequence
<220> FEATURE:
<223> OTHER INFORMATION: Synthetic

<400> SEQUENCE: 12

Gly Ala Met Ala Leu Pro Ser Gly Ser Asp Pro Ala Phe Ser Gln Pro
1               5                   10                  15

Lys Ser Val Leu Asp Ala Gly Leu Thr Cys Gln Gly Ala Ser Pro Ser
            20                  25                  30

Ser Val Ser Lys Pro Ile Leu Leu Val Pro Gly Thr Gly Thr Thr Gly
        35                  40                  45

Pro Gln Ser Phe Asp Ser Asn Trp Ile Pro Leu Ser Ala Gln Leu Gly
    50                  55                  60

Tyr Thr Pro Cys Trp Ile Ser Pro Pro Pro Phe Met Leu Asn Asp Thr
65                  70                  75                  80

Gln Val Asn Thr Glu Tyr Met Val Asn Ala Ile Thr Thr Leu Tyr Ala
                85                  90                  95

Gly Ser Gly Asn Asn Lys Leu Pro Val Leu Thr Ala Ser Gln Gly Gly
            100                 105                 110

Leu Val Ala Gln Trp Gly Leu Thr Phe Phe Pro Ser Ile Arg Ser Lys
        115                 120                 125

Val Asp Arg Leu Met Ala Phe Ala Pro Asp Tyr Lys Gly Thr Val Leu
    130                 135                 140

Ala Gly Pro Leu Asp Ala Leu Ala Val Ser Ala Pro Ser Val Trp Gln
145                 150                 155                 160

Gln Thr Thr Gly Ser Ala Leu Thr Thr Ala Leu Arg Asn Ala Gly Gly
                165                 170                 175

Leu Thr Gln Ile Val Pro Thr Thr Asn Leu Tyr Ser Ala Thr Asp Glu
            180                 185                 190

Val Val Gln Pro Gln Val Ser Asn Ser Pro Leu Asp Ser Ser Tyr Leu
        195                 200                 205

Phe Asn Gly Lys Asn Val Gln Ala Gln Ala Val Cys Gly Pro Leu Phe
    210                 215                 220

Val Ile Asp His Ala Gly Ser Leu Thr Ser Gln Phe Ser Tyr Val Val
225                 230                 235                 240

```
Gly Arg Ser Ala Leu Arg Ser Thr Thr Gly Gln Ala Arg Ser Ala Asp
                245                 250                 255

Tyr Gly Ile Thr Asp Cys Asn Pro Leu Pro Ala Asn Asp Leu Thr Pro
            260                 265                 270

Glu Gln Lys Val Ala Ala Ala Ala Leu Leu Ala Pro Ala Ala Ala Ala
            275                 280                 285

Ile Val Ala Gly Pro Lys Gln Asn Cys Glu Pro Asp Leu Met Pro Tyr
        290                 295                 300

Ala Arg Pro Phe Ala Val Gly Lys Arg Thr Cys Ser Gly Ile Val Thr
305                 310                 315                 320

Pro

<210> SEQ ID NO 13
<211> LENGTH: 321
<212> TYPE: PRT
<213> ORGANISM: Artificial Sequence
<220> FEATURE:
<223> OTHER INFORMATION: Synthetic

<400> SEQUENCE: 13

Gly Ala Met Ala Leu Pro Ser Gly Ser Asp Pro Ala Phe Ser Gln Pro
1               5                   10                  15

Lys Ser Val Leu Asp Ala Gly Leu Thr Cys Gln Gly Ala Ser Pro Ser
            20                  25                  30

Ser Val Ser Lys Pro Ile Leu Leu Val Pro Gly Thr Gly Thr Thr Gly
        35                  40                  45

Pro Gln Ser Phe Asp Ser Asn Trp Ile Pro Leu Ser Ala Gln Leu Gly
    50                  55                  60

Tyr Thr Pro Cys Trp Ile Ser Pro Pro Phe Met Leu Asn Asp Thr
65                  70                  75                  80

Gln Val Asn Thr Glu Tyr Met Val Asn Ala Ile Thr Thr Leu Tyr Ala
                85                  90                  95

Gly Ser Gly Asn Asn Lys Leu Pro Val Leu Thr Trp Ser Gln Gly Gly
            100                 105                 110

Leu Val Ala Gln Trp Gly Leu Thr Phe Phe Pro Ser Ile Arg Ser Lys
        115                 120                 125

Val Asp Arg Leu Met Ala Phe Ala Pro Asp Tyr Lys Gly Thr Val Leu
    130                 135                 140

Ala Gly Pro Leu Asp Ala Leu Ala Val Ser Ala Pro Ser Val Trp Gln
145                 150                 155                 160

Leu Thr Thr Gly Ser Ala Leu Thr Ala Leu Arg Asn Ala Gly Gly
                165                 170                 175

Leu Thr Gln Ile Val Pro Thr Thr Asn Leu Tyr Ser Ala Thr Asp Glu
            180                 185                 190

Ala Val Gln Pro Gln Val Ser Asn Ser Pro Leu Asp Ser Ser Tyr Leu
        195                 200                 205

Phe Asn Gly Lys Asn Val Gln Ala Gln Ala Val Cys Gly Pro Leu Phe
    210                 215                 220

Val Ile Asp His Ala Gly Ser Leu Thr Ser Gln Phe Ser Tyr Val Val
225                 230                 235                 240

Gly Arg Ser Ala Leu Arg Ser Thr Thr Gly Gln Ala Arg Ser Ala Asp
                245                 250                 255

Tyr Gly Ile Thr Asp Cys Asn Pro Leu Pro Ala Asn Asp Leu Thr Pro
            260                 265                 270

Glu Gln Lys Val Ala Ala Ala Ala Leu Leu Ala Pro Ala Ala Ala Ala
```

```
            275                 280                 285
Ile Val Ala Gly Pro Lys Gln Asn Cys Glu Pro Asp Leu Met Pro Tyr
290                 295                 300
Ala Arg Pro Phe Ala Val Gly Lys Arg Thr Cys Ser Gly Ile Val Thr
305                 310                 315                 320
Pro
```

<210> SEQ ID NO 14
<211> LENGTH: 321
<212> TYPE: PRT
<213> ORGANISM: Artificial Sequence
<220> FEATURE:
<223> OTHER INFORMATION: Synthetic

<400> SEQUENCE: 14

```
Gly Ala Met Ala Leu Pro Ser Gly Ser Asp Pro Ala Phe Ser Gln Pro
1               5                   10                  15
Lys Ser Val Leu Asp Ala Gly Leu Thr Cys Gln Gly Ala Ser Pro Ser
            20                  25                  30
Ser Val Ser Lys Pro Ile Leu Leu Val Pro Gly Thr Gly Thr Thr Gly
        35                  40                  45
Pro Gln Ser Phe Asp Ser Asn Trp Ile Pro Leu Ser Ala Gln Leu Gly
    50                  55                  60
Tyr Thr Pro Cys Trp Ile Ser Pro Pro Phe Met Leu Asn Asp Thr
65                  70                  75                  80
Gln Val Asn Thr Glu Tyr Met Val Asn Ala Ile Thr Thr Leu Tyr Ala
                85                  90                  95
Gly Ser Gly Asn Asn Lys Leu Pro Val Leu Thr Trp Ser Gln Gly Gly
            100                 105                 110
Leu Val Ala Gln Trp Gly Leu Thr Phe Phe Pro Ser Ile Arg Ser Lys
        115                 120                 125
Val Asp Arg Leu Met Ala Phe Ala Pro Asp Tyr Lys Gly Thr Val Leu
    130                 135                 140
Ala Gly Pro Leu Asp Ala Leu Ala Val Ser Ala Pro Ser Val Trp Gln
145                 150                 155                 160
Gln Thr Thr Gly Ser Ala Leu Thr Thr Ala Leu Arg Asn Ala Gly Gly
                165                 170                 175
Leu Thr Gln Ile Val Pro Thr Thr Asn Leu Tyr Ser Ala Thr Asp Glu
            180                 185                 190
Ile Cys Gln Pro Gln Val Ser Asn Ser Pro Leu Asp Ser Ser Tyr Leu
        195                 200                 205
Phe Asn Gly Lys Asn Val Gln Ala Gln Ala Val Cys Gly Pro Leu Phe
    210                 215                 220
Val Ile Asp His Ala Gly Ser Leu Thr Ser Gln Phe Ser Tyr Val Val
225                 230                 235                 240
Gly Arg Ser Ala Leu Arg Ser Thr Thr Gly Gln Ala Arg Ser Ala Asp
                245                 250                 255
Tyr Gly Ile Thr Asp Cys Asn Pro Leu Pro Ala Asn Asp Leu Thr Pro
            260                 265                 270
Glu Gln Lys Val Ala Ala Ala Leu Leu Ala Pro Gly Val Ala Ala
        275                 280                 285
Ile Val Ala Gly Pro Lys Gln Asn Cys Glu Pro Asp Leu Met Pro Tyr
290                 295                 300
Ala Arg Pro Phe Ala Val Gly Lys Arg Thr Cys Ser Gly Ile Val Thr
305                 310                 315                 320
```

Pro

<210> SEQ ID NO 15
<211> LENGTH: 342
<212> TYPE: PRT
<213> ORGANISM: Artificial Sequence
<220> FEATURE:
<223> OTHER INFORMATION: Synthetic

<400> SEQUENCE: 15

Met Lys Leu Leu Ser Leu Thr Gly Val Ala Gly Val Leu Ala Thr Cys
1               5                   10                  15

Val Ala Ala Thr Pro Leu Val Lys Arg Leu Pro Ser Gly Ser Asp Pro
            20                  25                  30

Ala Phe Ser Gln Pro Lys Ser Val Leu Asp Ala Gly Leu Thr Cys Gln
        35                  40                  45

Gly Thr Ser Pro Thr Ser Val Thr Lys Pro Ile Leu Leu Val Pro Gly
    50                  55                  60

Thr Gly Thr Thr Gly Pro Gly Ser Phe Asp Ser Asn Trp Ile Pro Leu
65                  70                  75                  80

Ser Thr Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
            100                 105                 110

Thr Thr Leu Tyr Ala Gly Ser Gly Asn Arg Lys Leu Pro Val Leu Thr
        115                 120                 125

Trp Ser Gln Gly Gly Leu Val Ala Gln Trp Gly Leu Thr Phe Phe Pro
    130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175

Pro Ser Val Trp Gln Gln Thr Thr Gly Ser Ala Leu Thr Thr Ala Leu
            180                 185                 190

Arg Asn Ala Gly Gly Leu Thr Gln Ile Val Pro Thr Thr Asn Leu Tyr
        195                 200                 205

Ser Ala Thr Asp Glu Ile Val Gln Pro Gln Val Ser Asn Ser Pro Leu
    210                 215                 220

Asp Ser Ser Tyr Leu Phe Asn Gly Lys Asn Val Gln Ala Gln Ala Val
225                 230                 235                 240

Cys Gly Pro Leu Phe Val Ile Asp His Ala Gly Ser Leu Thr Ser Gln
                245                 250                 255

Phe Ser Tyr Val Val Gly Arg Ser Ala Leu Arg Ser Thr Thr Gly Gln
            260                 265                 270

Ala Arg Ser Ala Asp Tyr Gly Ile Thr Asp Cys Asn Pro Leu Pro Ala
        275                 280                 285

Asn Asp Leu Thr Pro Glu Gln Lys Val Ala Ala Ala Leu Leu Ala
    290                 295                 300

Pro Ala Ala Ala Ala Ile Ile Ala Gly Pro Lys Gln Asn Cys Glu Pro
305                 310                 315                 320

Asp Leu Met Pro Tyr Ala Arg Pro Phe Ala Val Gly Lys Arg Thr Cys
                325                 330                 335

Ser Gly Ile Val Thr Pro
            340

```
<210> SEQ ID NO 16
<211> LENGTH: 342
<212> TYPE: PRT
<213> ORGANISM: Artificial Sequence
<220> FEATURE:
<223> OTHER INFORMATION: Synthetic

<400> SEQUENCE: 16

Met Lys Leu Leu Ser Val Ser Gly Ile Val Gly Val Leu Ala Thr Cys
1               5                   10                  15

Val Ala Ala Thr Pro Leu Val Lys Arg Leu Pro Thr Gly Ser Asp Pro
            20                  25                  30

Ala Phe Ser Gln Pro Lys Ser Val Leu Asp Ala Gly Leu Thr Cys Gln
        35                  40                  45

Gly Thr Ser Pro Thr Ser Val Thr Lys Pro Ile Leu Leu Val Pro Gly
    50                  55                  60

Thr Gly Thr Thr Gly Pro Gly Ser Phe Asp Ser Asn Trp Ile Pro Leu
65                  70                  75                  80

Ser Thr Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
            100                 105                 110

Thr Thr Leu Tyr Ala Gly Ser Gly Asn Arg Lys Leu Pro Val Leu Thr
        115                 120                 125

Trp Ser Gln Gly Gly Leu Val Ala Gln Trp Gly Leu Thr Phe Phe Pro
    130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175

Pro Ser Val Trp Gln Gln Thr Thr Gly Ser Ala Leu Thr Thr Ala Leu
            180                 185                 190

Arg Asn Ala Gly Gly Leu Thr Gln Ile Val Pro Thr Thr Asn Leu Tyr
        195                 200                 205

Ser Ala Thr Asp Glu Ile Val Gln Pro Gln Val Ser Asn Ser Pro Leu
    210                 215                 220

Asp Ser Ser Tyr Leu Phe Asn Gly Lys Asn Val Gln Ala Gln Ala Val
225                 230                 235                 240

Cys Gly Pro Leu Phe Val Ile Asp His Ala Gly Ser Leu Thr Ser Gln
                245                 250                 255

Phe Ser Tyr Val Val Gly Arg Ser Ala Leu Arg Ser Thr Thr Gly Gln
            260                 265                 270

Ala Arg Ser Ala Asp Tyr Gly Ile Thr Asp Cys Asn Pro Leu Pro Ala
        275                 280                 285

Asn Asp Leu Thr Pro Glu Gln Lys Val Ala Ala Ala Leu Leu Ala
    290                 295                 300

Pro Ala Ala Ala Ala Ile Ile Ala Gly Pro Lys Gln Asn Cys Glu Pro
305                 310                 315                 320

Asp Leu Met Pro Tyr Ala Arg Pro Phe Ala Val Gly Lys Arg Thr Cys
                325                 330                 335

Ser Gly Ile Val Thr Pro
            340

<210> SEQ ID NO 17
<211> LENGTH: 321
```

<212> TYPE: PRT
<213> ORGANISM: Artificial Sequence
<220> FEATURE:
<223> OTHER INFORMATION: Synthetic

<400> SEQUENCE: 17

```
Gly Ala Met Ala Leu Pro Ser Gly Ser Asp Pro Ala Phe Ser Gln Pro
1               5                   10                  15

Lys Ser Val Leu Asp Ala Gly Leu Thr Cys Gln Gly Ala Ser Pro Ser
            20                  25                  30

Ser Val Ser Lys Pro Ile Leu Leu Val Pro Gly Thr Gly Thr Thr Gly
        35                  40                  45

Pro Gln Ser Phe Asp Ser Asn Trp Ile Pro Leu Ser Ala Gln Leu Gly
    50                  55                  60

Tyr Thr Pro Cys Trp Ile Ser Pro Pro Phe Met Leu Asn Asp Thr
65                  70                  75                  80

Gln Val Asn Thr Glu Tyr Met Val Asn Ala Ile Thr Thr Leu Tyr Ala
                85                  90                  95

Gly Ser Gly Asn Asn Lys Leu Pro Val Leu Thr Ala Ser Gln Gly Gly
            100                 105                 110

Leu Val Ala Gln Trp Gly Leu Thr Phe Phe Pro Ser Ile Arg Ser Lys
        115                 120                 125

Val Asp Arg Leu Met Ala Phe Ala Pro Leu Tyr Lys Gly Thr Val Leu
130                 135                 140

Ala Gly Pro Leu Asp Ala Leu Ala Val Ser Ala Pro Ser Val Trp Gln
145                 150                 155                 160

Gln Thr Thr Gly Ser Ala Leu Thr Thr Ala Leu Arg Asn Ala Gly Gly
                165                 170                 175

Leu Thr Gln Ile Val Pro Thr Thr Asn Leu Tyr Ser Ala Thr Asp Glu
            180                 185                 190

Met Cys Gln Pro Gln Val Ser Asn Ser Pro Leu Asp Ser Ser Tyr Leu
        195                 200                 205

Phe Asn Gly Lys Asn Val Gln Ala Gln Ala Val Cys Gly Pro Leu Phe
210                 215                 220

Val Ile Asp His Ala Gly Ser Leu Thr Ser Gln Phe Ser Tyr Val Val
225                 230                 235                 240

Gly Arg Ser Ala Leu Arg Ser Thr Thr Gly Gln Ala Arg Ser Ala Asp
                245                 250                 255

Tyr Gly Ile Thr Asp Cys Asn Pro Leu Pro Ala Asn Asp Leu Thr Pro
            260                 265                 270

Glu Gln Lys Val Ala Ala Ala Leu Leu Ala Pro Ala Ala Ala
        275                 280                 285

Ile Val Ala Gly Pro Lys Gln Asn Cys Glu Pro Asp Leu Met Pro Tyr
290                 295                 300

Ala Arg Pro Phe Ala Val Gly Lys Arg Thr Cys Ser Gly Ile Val Thr
305                 310                 315                 320

Pro
```

<210> SEQ ID NO 18
<211> LENGTH: 321
<212> TYPE: PRT
<213> ORGANISM: Artificial Sequence
<220> FEATURE:
<223> OTHER INFORMATION: Synthetic

<400> SEQUENCE: 18

-continued

```
Gly Ala Met Ala Leu Pro Ser Gly Ser Asp Pro Ala Phe Ser Gln Pro
1               5                   10                  15

Lys Ser Val Leu Asp Ala Gly Leu Thr Cys Gln Gly Ala Ser Pro Ser
            20                  25                  30

Ser Val Ser Lys Pro Ile Leu Leu Val Pro Gly Thr Gly Thr Thr Gly
        35                  40                  45

Pro Gln Ser Phe Asp Ser Asn Trp Ile Pro Leu Ser Ala Gln Leu Gly
    50                  55                  60

Tyr Thr Pro Cys Trp Ile Ser Pro Pro Phe Met Leu Asn Asp Thr
65                  70                  75                  80

Gln Val Asn Thr Glu Tyr Met Val Asn Ala Ile Thr Thr Leu Tyr Ala
                85                  90                  95

Gly Ser Gly Asn Asn Lys Leu Pro Val Leu Thr Val Ser Gln Gly Gly
            100                 105                 110

Leu Val Ala Gln Trp Gly Leu Thr Phe Phe Pro Ser Ile Arg Ser Lys
        115                 120                 125

Val Asp Arg Leu Met Ala Phe Ala Pro Asp Tyr Lys Gly Thr Val Leu
    130                 135                 140

Ala Gly Pro Leu Asp Ala Leu Ala Gly Ser Ala Pro Ser Val Trp Gln
145                 150                 155                 160

Gln Thr Thr Gly Ser Ala Leu Thr Thr Ala Leu Arg Asn Ala Gly Gly
                165                 170                 175

Leu Thr Gln Ile Val Pro Thr Thr Asn Leu Tyr Ser Ala Thr Asp Glu
            180                 185                 190

Ile Val Gln Pro Gln Val Ser Asn Ser Pro Leu Asp Ser Ser Tyr Leu
        195                 200                 205

Phe Asn Gly Lys Asn Val Gln Ala Gln Ala Val Cys Gly Pro Leu Phe
    210                 215                 220

Val Ile Asp His Ala Gly Ser Leu Thr Ser Gln Phe Ser Tyr Val Val
225                 230                 235                 240

Gly Arg Ser Ala Leu Arg Ser Thr Thr Gly Gln Ala Arg Ser Ala Asp
                245                 250                 255

Tyr Gly Ile Thr Asp Cys Asn Pro Leu Pro Ala Asn Asp Leu Thr Pro
            260                 265                 270

Glu Gln Lys Val Ala Ala Ala Leu Leu Ala Pro Tyr Tyr Ala Ala
        275                 280                 285

Ile Val Ala Gly Pro Lys Gln Asn Cys Glu Pro Asp Leu Met Pro Tyr
    290                 295                 300

Ala Arg Pro Phe Ala Val Gly Lys Arg Thr Cys Ser Gly Ile Val Thr
305                 310                 315                 320

Pro
```

<210> SEQ ID NO 19
<211> LENGTH: 321
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (109)..(109)
<223> OTHER INFORMATION: Xaa can be any naturally occurring amino acid

<400> SEQUENCE: 19

```
Gly Ala Met Ala Leu Pro Ser Gly Ser Asp Pro Ala Phe Ser Gln Pro
1               5                   10                  15
```

```
Lys Ser Val Leu Asp Ala Gly Leu Thr Cys Gln Gly Ala Ser Pro Ser
            20                  25                  30

Ser Val Ser Lys Pro Ile Leu Leu Val Pro Gly Thr Gly Thr Thr Gly
        35                  40                  45

Pro Gln Ser Phe Asp Ser Asn Trp Ile Pro Leu Ser Ala Gln Leu Gly
    50                  55                  60

Tyr Thr Pro Cys Trp Ile Ser Pro Pro Phe Met Leu Asn Asp Thr
65                  70                  75                  80

Gln Val Asn Thr Glu Tyr Met Val Asn Ala Ile Thr Thr Leu Tyr Ala
                85                  90                  95

Gly Ser Gly Asn Asn Lys Leu Pro Val Leu Thr Val Xaa Gln Gly Gly
            100                 105                 110

Leu Val Ala Gln Trp Gly Leu Thr Phe Phe Pro Ser Ile Arg Ser Lys
        115                 120                 125

Val Asp Arg Leu Met Ala Phe Ala Pro Asp Tyr Lys Gly Thr Val Leu
    130                 135                 140

Ala Gly Pro Leu Asp Ala Leu Ala Gly Ser Ala Pro Ser Val Trp Gln
145                 150                 155                 160

Gln Thr Thr Gly Ser Ala Leu Thr Thr Ala Leu Arg Asn Ala Gly Gly
                165                 170                 175

Leu Thr Gln Ile Val Pro Thr Thr Asn Leu Tyr Ser Ala Thr Asp Glu
            180                 185                 190

Ile Val Gln Pro Gln Val Ser Asn Ser Pro Leu Asp Ser Ser Tyr Leu
        195                 200                 205

Phe Asn Gly Lys Asn Val Gln Ala Gln Ala Val Cys Gly Pro Leu Phe
    210                 215                 220

Val Ile Asp His Ala Gly Ser Leu Thr Ser Gln Phe Ser Tyr Val Val
225                 230                 235                 240

Gly Arg Ser Ala Leu Arg Ser Thr Thr Gly Gln Ala Arg Ser Ala Asp
                245                 250                 255

Tyr Gly Ile Thr Asp Cys Asn Pro Leu Pro Ala Asn Asp Leu Thr Pro
            260                 265                 270

Glu Gln Lys Val Ala Ala Ala Leu Leu Ala Pro Tyr Tyr Ala Ala
        275                 280                 285

Ile Val Ala Gly Pro Lys Gln Asn Cys Glu Pro Asp Leu Met Pro Tyr
    290                 295                 300

Ala Arg Pro Phe Ala Val Gly Lys Arg Thr Cys Ser Gly Ile Val Thr
305                 310                 315                 320

Pro

<210> SEQ ID NO 20
<211> LENGTH: 321
<212> TYPE: PRT
<213> ORGANISM: Artificial Sequence
<220> FEATURE:
<223> OTHER INFORMATION: Synthetic

<400> SEQUENCE: 20

Gly Ala Met Ala Leu Pro Ser Gly Ser Asp Pro Ala Phe Ser Gln Pro
1               5                   10                  15

Lys Ser Val Leu Asp Ala Gly Leu Thr Cys Gln Gly Ala Ser Pro Ser
            20                  25                  30

Ser Val Ser Lys Pro Ile Leu Leu Val Pro Gly Thr Gly Thr Thr Gly
        35                  40                  45

Pro Gln Ser Phe Asp Ser Asn Trp Ile Pro Leu Ser Ala Gln Leu Gly
```

```
              50                  55                  60
Tyr Thr Pro Cys Trp Ile Ser Pro Pro Phe Met Leu Asn Asp Thr
 65                  70                  75                  80

Gln Val Asn Thr Glu Tyr Met Val Asn Ala Ile Thr Thr Leu Tyr Ala
                 85                  90                  95

Gly Ser Gly Asn Asn Lys Leu Pro Val Leu Thr Val Cys Gln Gly Gly
                100                 105                 110

Leu Val Ala Gln Trp Gly Leu Thr Phe Phe Pro Ser Ile Arg Ser Lys
                115                 120                 125

Val Asp Arg Leu Met Ala Phe Ala Pro Asp Tyr Lys Gly Thr Val Leu
            130                 135                 140

Ala Gly Pro Leu Asp Ala Leu Ala Gly Ser Ala Pro Ser Val Trp Gln
145                 150                 155                 160

Gln Thr Thr Gly Ser Ala Leu Thr Ala Leu Arg Asn Ala Gly Gly
                165                 170                 175

Leu Thr Gln Ile Val Pro Thr Thr Asn Leu Tyr Ser Ala Thr Asp Glu
                180                 185                 190

Ile Val Gln Pro Gln Val Ser Asn Ser Pro Leu Asp Ser Ser Tyr Leu
                195                 200                 205

Phe Asn Gly Lys Asn Val Gln Ala Gln Ala Val Cys Gly Pro Leu Phe
210                 215                 220

Val Ile Asp His Ala Gly Ser Leu Thr Ser Gln Phe Ser Tyr Val Val
225                 230                 235                 240

Gly Arg Ser Ala Leu Arg Ser Thr Thr Gly Gln Ala Arg Ser Ala Asp
                245                 250                 255

Tyr Gly Ile Thr Asp Cys Asn Pro Leu Pro Ala Asn Asp Leu Thr Pro
                260                 265                 270

Glu Gln Lys Val Ala Ala Ala Leu Leu Ala Pro Tyr Tyr Ala Ala
                275                 280                 285

Ile Val Ala Gly Pro Lys Gln Asn Cys Glu Pro Asp Leu Met Pro Tyr
                290                 295                 300

Ala Arg Pro Phe Ala Val Gly Lys Arg Thr Cys Ser Gly Ile Val Thr
305                 310                 315                 320

Pro

<210> SEQ ID NO 21
<211> LENGTH: 316
<212> TYPE: PRT
<213> ORGANISM: Artificial Sequence
<220> FEATURE:
<223> OTHER INFORMATION: Synthetic

<400> SEQUENCE: 21

Ala Ala Ile Val Ala Gly Pro Lys Gln Asn Cys Glu Pro Asp Leu Met
 1               5                  10                  15

Pro Tyr Ala Arg Pro Phe Ala Val Gly Lys Arg Thr Cys Ser Gly Ile
                20                  25                  30

Val Gly Leu Pro Ser Gly Ser Asp Pro Ala Phe Ser Gln Pro Lys Ser
                35                  40                  45

Val Leu Asp Ala Gly Leu Thr Cys Gln Gly Ala Ser Pro Ser Ser Val
            50                  55                  60

Ser Lys Pro Ile Leu Leu Val Pro Gly Thr Gly Thr Gly Pro Gln
 65                  70                  75                  80

Ser Phe Asp Ser Asn Trp Ile Pro Leu Ser Ala Gln Leu Gly Tyr Thr
                85                  90                  95
```

```
Pro Cys Trp Ile Ser Pro Pro Phe Met Leu Asn Asp Thr Gln Val
            100                 105                 110

Asn Thr Glu Tyr Met Val Asn Ala Ile Thr Thr Leu Tyr Ala Gly Ser
    115                 120                 125

Gly Asn Asn Lys Leu Pro Val Leu Thr Trp Ser Gln Gly Gly Leu Val
130                 135                 140

Ala Gln Trp Gly Leu Thr Phe Phe Pro Ser Ile Arg Ser Lys Val Asp
145                 150                 155                 160

Arg Leu Met Ala Phe Ala Pro Asp Tyr Lys Gly Thr Val Leu Ala Gly
                165                 170                 175

Pro Leu Asp Ala Leu Ala Val Ser Ala Pro Ser Val Trp Gln Gln Thr
            180                 185                 190

Thr Gly Ser Ala Leu Thr Thr Ala Leu Arg Asn Ala Gly Gly Leu Thr
        195                 200                 205

Gln Ile Val Pro Thr Thr Asn Leu Tyr Ser Ala Thr Asp Glu Ile Val
    210                 215                 220

Gln Pro Gln Val Ser Asn Ser Pro Leu Asp Ser Ser Tyr Leu Phe Asn
225                 230                 235                 240

Gly Lys Asn Val Gln Ala Gln Ala Val Cys Gly Pro Leu Phe Val Ile
                245                 250                 255

Asp His Ala Gly Ser Leu Thr Ser Gln Phe Ser Tyr Val Val Gly Arg
            260                 265                 270

Ser Ala Leu Arg Ser Thr Thr Gly Gln Ala Arg Ser Ala Asp Tyr Gly
        275                 280                 285

Ile Thr Asp Cys Asn Pro Leu Pro Ala Asn Asp Leu Thr Pro Glu Gln
    290                 295                 300

Lys Val Ala Ala Ala Leu Leu Ala Pro Ala Ala
305                 310                 315

<210> SEQ ID NO 22
<211> LENGTH: 331
<212> TYPE: PRT
<213> ORGANISM: Artificial Sequence
<220> FEATURE:
<223> OTHER INFORMATION: Synthetic

<400> SEQUENCE: 22

Leu Leu Ala Gly Ala Val Val Gly Thr Pro Leu Val Lys Arg Leu Pro
1               5                   10                  15

Gly Gly Ser Asp Pro Ala Phe Thr Gln Pro Gln Ala Val Leu Asp Ala
                20                  25                  30

Gly Leu Thr Cys Gln Gly Ala Ser Pro Ser Ser Val Ser Asn Pro Ile
            35                  40                  45

Leu Leu Val Pro Gly Thr Gly Thr Thr Gly Pro Gly Ser Phe Asp Ser
        50                  55                  60

Asn Trp Ile Pro Leu Ser Thr Gln Leu Gly Tyr Thr Pro Cys Trp Ile
65                  70                  75                  80

Ser Pro Pro Pro Phe Met Leu Asn Asp Thr Gln Val Asn Ala Glu Tyr
                85                  90                  95

Met Val Asn Ala Val Thr Lys Leu Tyr Ala Gly Ser Gly Asn Lys Ala
                100                 105                 110

Val Pro Val Leu Thr Trp Ser Gln Gly Gly Leu Val Ala Gln Trp Gly
            115                 120                 125

Leu Thr Phe Phe Pro Ser Ile Arg Gly Lys Val Asp Arg Leu Met Ala
        130                 135                 140
```

-continued

```
Phe Ala Pro Asp Tyr Lys Gly Thr Val Leu Ala Gly Ile Leu Asp Ala
145                 150                 155                 160

Leu Ser Val Ala Ala Pro Ser Val Trp Gln Gln Thr Ala Gly Ser Ala
                165                 170                 175

Leu Thr Thr Ala Leu Lys Asn Ala Gly Gly Leu Thr Gln Ile Val Pro
            180                 185                 190

Thr Thr Asn Leu Tyr Ser Ala Thr Asp Glu Val Val Gln Pro Gln Val
        195                 200                 205

Ser Asn Ser Pro Leu Asp Ser Ser Tyr Leu Phe Asn Ala Lys Asn Val
    210                 215                 220

Gln Ala Gln Ser Val Cys Gly Pro Leu Phe Val Ile Asp His Ala Gly
225                 230                 235                 240

Ser Leu Thr Ser Gln Phe Ser Tyr Val Val Gly Arg Ser Ala Leu Arg
                245                 250                 255

Ser Thr Ser Gly Gln Ala Arg Ser Ser Asp Tyr Ser Ile Thr Asp Cys
            260                 265                 270

Asn Pro Leu Pro Ala Asn Asp Leu Thr Pro Glu Gln Lys Val Ala Ala
        275                 280                 285

Ala Ala Leu Leu Val Pro Ala Ala Ala Ile Ala Ala Gly Pro Lys
    290                 295                 300

Gln Asn Cys Glu Pro Asp Leu Met Pro Tyr Ala Arg Arg Tyr Ala Val
305                 310                 315                 320

Gly Lys Ile Thr Cys Ser Gly Ile Val Thr Pro
                325                 330
```

<210> SEQ ID NO 23
<211> LENGTH: 343
<212> TYPE: PRT
<213> ORGANISM: Artificial Sequence
<220> FEATURE:
<223> OTHER INFORMATION: Synthetic

<400> SEQUENCE: 23

```
Met Lys Phe Ser Thr Leu Ala Ser Leu Val Ala Ile Ala Ala Ser Ala
1               5                   10                  15

Val Thr Ala Thr Pro Leu Val Glu Arg Leu Pro Gln Gly Ser Asp Pro
                20                  25                  30

Ala Phe Ser Thr Pro Lys Ser Val Leu Asp Ala Gly Leu Thr Cys Lys
            35                  40                  45

Asn Gly Ser Pro Ser Ser Gln Thr Lys Pro Ile Leu Leu Val Pro Gly
        50                  55                  60

Thr Gly Val Thr Gly Glu Gln Asn Tyr Asp Ser Asn Trp Ile Pro Leu
65                  70                  75                  80

Ser Ser Ala Leu Gly Tyr Ser Pro Cys Trp Val Ser Pro Pro Pro Phe
                85                  90                  95

Met Leu Asn Asp Ser Gln Val Asn Ala Glu Tyr Ile Val Asn Ala Val
            100                 105                 110

Asn Val Leu Tyr Ala Gly Asn Gly Asn Lys Lys Val Pro Val Leu Thr
        115                 120                 125

Trp Ser Gln Gly Gly Leu Ala Thr Gln Trp Gly Leu Thr Phe Phe Pro
    130                 135                 140

Ser Ile Arg Ser Lys Val Asp Arg Leu Met Ala Phe Ala Pro Asp Tyr
145                 150                 155                 160

Lys Gly Thr Ile Glu Ala Ser Phe Leu Asn Ala Val Gly Leu Ser Ser
                165                 170                 175
```

Gln Ser Ile Trp Gln Gln Thr Ser Gly Ser Ala Tyr Leu Thr Ala Leu
            180                 185                 190

Met Asn Ala Gly Gly Leu Asn Gln Ile Val Pro Thr Asn Leu Tyr
            195                 200                 205

Ser Ala Thr Asp Glu Ile Val Gln Pro Gln Ile Thr Asn Ser Pro Leu
    210                 215                 220

Asp Ser Ser Tyr Leu Phe Asn Ala Lys Asn Ile Gln Ala Gln Thr Val
225                 230                 235                 240

Cys Gly Pro Leu Phe Ile Ile Asp His Ala Gly Ser Val Thr Ser Gln
                245                 250                 255

Phe Ser Tyr Val Val Gly Lys Ser Ala Leu Gly Ser Pro Thr Gly Gln
            260                 265                 270

Ala Gln Ser Ser Asp Tyr Gly Leu Thr Asp Cys Asn Pro Leu Pro Ala
        275                 280                 285

Asn Asp Leu Thr Ala Glu Gln Lys Leu Glu Ser Ser Gly Leu Leu Leu
    290                 295                 300

Val Ala Gly Ala Asn Val Ile Ala Gly Pro Lys Gln Asn Cys Glu Pro
305                 310                 315                 320

Asp Leu Lys Pro Tyr Ala Arg Arg Tyr Ala Ile Gly Lys Arg Thr Cys
                325                 330                 335

Ser Gly Phe Val Thr Pro Phe
            340

<210> SEQ ID NO 24
<211> LENGTH: 475
<212> TYPE: PRT
<213> ORGANISM: Artificial Sequence
<220> FEATURE:
<223> OTHER INFORMATION: Synthetic

<400> SEQUENCE: 24

Met Lys Val Ser Leu Val Lys Ile Ala Phe Thr Ala Leu Met Val Ser
1               5                   10                  15

Gly Ile Ser Ala His Pro Thr Lys Glu Leu Glu Arg Arg Asp Leu Ile
            20                  25                  30

Ser Asn Ile Asp Asp Ile Val Asn Ser Thr Ile Asp Asn Gly Glu Ala
        35                  40                  45

His Lys Asp Asn Ala Lys Ser Ala Ile Thr Asp Ile Phe Asp Lys Ile
    50                  55                  60

Asn Asp Gly Ile Lys Gln Asp Ile Asp Asn Leu Lys Glu Val Gly Lys
65                  70                  75                  80

Ser Ile Ala Asp Leu Ile Lys Ser Val Val Pro Thr Glu Asp Leu Ser
                85                  90                  95

Thr Pro Glu Gly Val Gln Ala Tyr Leu Gly Gln Leu Phe Glu Asn Gly
            100                 105                 110

Glu Asp Leu Phe Lys Asn Ser Ile Asp Met Val Gly His Gly Leu Lys
        115                 120                 125

Pro Gly Ser Ile Ala Gly Asn Phe Glu Gly Phe Ser Asp Glu Ile Asn
    130                 135                 140

Thr Ser Asp Asn Phe Asn Val Lys Glu Pro Glu Gly Ser Val Tyr Pro
145                 150                 155                 160

Gln Ala Glu Ser Glu Asp Pro Ser Phe Ser Leu Ser Glu Gly Gln Leu
                165                 170                 175

Arg Ser Ala Ile Gln Ile Pro Glu Glu Phe Gln Tyr Gly Asn Gly Ser
            180                 185                 190

Lys Ser Pro Val Ile Leu Val Pro Gly Thr Gly Ser Lys Gly Gly Met
            195                 200                 205

Thr Tyr Ala Ser Asn Tyr Ala Lys Leu Leu Lys Glu Thr Asp Phe Ala
        210                 215                 220

Asp Val Val Trp Leu Asn Val Pro Gly Tyr Leu Leu Asp Asp Ala Gln
225                 230                 235                 240

Asn Asn Ala Glu Tyr Val Ala Tyr Ala Ile Asn Tyr Ile Ser Gly Ile
                245                 250                 255

Ser Asn Asn Lys Asn Val Ser Ile Ile Ser Trp Ser Gln Gly Gly Leu
                260                 265                 270

Asp Thr Gln Trp Ala Leu Lys Tyr Trp Ala Ser Thr Arg Ser Lys Val
                275                 280                 285

Ser Asp Phe Ile Pro Ile Ser Pro Asp Phe Lys Gly Thr Arg Met Val
            290                 295                 300

Pro Val Leu Cys Pro Ser Phe Pro Lys Leu Ser Cys Pro Pro Ser Val
305                 310                 315                 320

Leu Gln Gln Glu Tyr Asn Ser Thr Phe Ile Glu Thr Leu Arg Ala Asp
                325                 330                 335

Gly Gly Asp Ser Ala Tyr Val Pro Thr Thr Ser Ile Tyr Ser Gly Phe
                340                 345                 350

Asp Glu Ile Val Gln Pro Gln Ser Gly Lys Gly Ala Ser Gly Leu Ile
            355                 360                 365

Asn Asp Asn Arg Asn Val Gly Val Thr Asn Asn Glu Val Gln Thr Ile
            370                 375                 380

Cys Pro Asp Arg Pro Ala Gly Lys Tyr Tyr Thr His Glu Gly Val Leu
385                 390                 395                 400

Tyr Asn Pro Val Gly Tyr Ala Leu Ala Val Asp Ala Leu Thr His Glu
                405                 410                 415

Gly Pro Gly Gln Leu Ser Arg Ile Asp Leu Asp Thr Glu Cys Gly Arg
            420                 425                 430

Ile Val Pro Asp Gly Leu Thr Tyr Thr Asp Leu Leu Ala Thr Glu Ala
            435                 440                 445

Leu Ile Pro Glu Ala Leu Val Leu Ile Leu Ser Tyr Asp Asp Lys Thr
        450                 455                 460

Arg Asp Glu Pro Glu Ile Arg Ser Tyr Ala Gln
465                 470                 475

<210> SEQ ID NO 25
<211> LENGTH: 463
<212> TYPE: PRT
<213> ORGANISM: Artificial Sequence
<220> FEATURE:
<223> OTHER INFORMATION: Synthetic

<400> SEQUENCE: 25

Met Arg Trp Ser Ser Leu Leu Lys Ala Ala Val Leu Tyr Arg Ala Ile
1               5                   10                  15

Leu Ser Pro Leu Val Ser Gly Ala Val Ile Pro Arg Gly Ala Val Pro
            20                  25                  30

Val Ala Ser Asp Leu Ser Leu Val Ser Ile Leu Ser Ser Ala Ala Asn
        35                  40                  45

Asp Ser Ser Ile Glu Ser Glu Ala Arg Ser Ile Ala Ser Leu Ile Ala
    50                  55                  60

Ser Glu Ile Val Ser Lys Ile Gly Lys Thr Glu Phe Ser Arg Ser Thr
65                  70                  75                  80

Lys Asp Ala Lys Ser Val Gln Glu Ala Phe Asp Lys Ile Gln Ser Ile
                85                  90                  95

Phe Ala Asp Gly Thr Pro Asp Phe Leu Lys Met Thr Arg Glu Ile Leu
            100                 105                 110

Thr Val Gly Leu Ile Pro Ala Asp Ile Val Ser Phe Leu Asn Gly Tyr
        115                 120                 125

Leu Asn Leu Asp Leu Asn Ser Ile His Asn Arg Asn Pro Ser Pro Lys
130                 135                 140

Gly Gln Ala Ile Tyr Pro Val Lys Ala Pro Gly Asp Ala Arg Tyr Ser
145                 150                 155                 160

Val Ala Glu Asn Ala Leu Arg Ala Ala Ile His Ile Pro Ala Ser Phe
                165                 170                 175

Gly Tyr Gly Lys Asn Gly Lys Lys Pro Val Ile Leu Val Pro Gly Thr
            180                 185                 190

Ala Thr Pro Ala Gly Thr Thr Tyr Tyr Phe Asn Phe Gly Lys Leu Gly
        195                 200                 205

Ser Ala Ala Asp Ala Asp Val Val Trp Leu Asn Ile Pro Gln Ala Ser
210                 215                 220

Leu Asn Asp Val Gln Ile Asn Ser Glu Tyr Val Ala Tyr Ala Ile Asn
225                 230                 235                 240

Tyr Ile Ser Ala Ile Ser Glu Ser Asn Val Ala Val Leu Ser Trp Ser
                245                 250                 255

Gln Gly Gly Leu Asp Thr Gln Trp Ala Leu Lys Tyr Trp Pro Ser Thr
            260                 265                 270

Arg Lys Val Val Asp Asp Phe Ile Ala Ile Ser Pro Asp Phe His Gly
        275                 280                 285

Thr Val Met Arg Ser Leu Val Cys Pro Trp Leu Ala Ala Leu Ala Cys
290                 295                 300

Thr Pro Ser Leu Trp Gln Gln Gly Trp Asn Thr Glu Phe Ile Arg Thr
305                 310                 315                 320

Leu Arg Gly Gly Gly Gly Asp Ser Ala Tyr Val Pro Thr Thr Thr Ile
                325                 330                 335

Tyr Ser Thr Phe Asp Glu Ile Val Gln Pro Met Ser Gly Ser Gln Ala
            340                 345                 350

Ser Ala Ile Leu Ser Asp Ser Arg Ala Val Gly Val Ser Asn Asn His
        355                 360                 365

Leu Gln Thr Ile Cys Gly Gly Lys Pro Ala Gly Gly Val Tyr Thr His
370                 375                 380

Glu Gly Val Leu Tyr Asn Pro Leu Ala Trp Ala Leu Ala Val Asp Ala
385                 390                 395                 400

Leu Ser His Asp Gly Pro Gly Asp Pro Ser Arg Leu Asp Leu Asp Val
                405                 410                 415

Val Cys Gly Arg Val Leu Pro Pro Gln Leu Gly Leu Asp Asp Leu Leu
            420                 425                 430

Gly Thr Glu Gly Leu Leu Leu Ile Ala Leu Ala Glu Val Leu Ala Tyr
        435                 440                 445

Lys Pro Lys Thr Phe Gly Glu Pro Ala Ile Ala Ser Tyr Ala His
450                 455                 460

<210> SEQ ID NO 26
<211> LENGTH: 420
<212> TYPE: PRT
<213> ORGANISM: Artificial Sequence
<220> FEATURE:

<223> OTHER INFORMATION: Synthetic

<400> SEQUENCE: 26

```
Met Arg Phe Phe Thr Ala Leu Ser Leu Phe Ile Ser Gly Ala Ala Ile
1               5                   10                  15

Ala Ser Ala Leu Pro Ser Ser Ser Glu Thr Val Glu Ala Asn Cys Val
            20                  25                  30

Lys Pro Tyr Leu Cys Cys Gly Glu Leu Lys Thr Pro Leu Asp Ser Thr
        35                  40                  45

Leu Asp Pro Ile Leu Leu Asp Leu Gly Ile Asp Ala Ala Ser Ile Val
    50                  55                  60

Gly Ser Val Gly Leu Leu Cys Leu Ile Pro Ser Lys Ala Leu Thr Cys
65                  70                  75                  80

Leu Asn Gly Tyr Ala Ile Ile Asp Leu Asn Ser Ile His Arg His Asn
                85                  90                  95

Pro Ser Pro Glu Asn Leu Ser Ile Tyr Pro Tyr Lys Ala Lys Ser Asp
            100                 105                 110

Ala Pro Tyr Ser Ile Ala Glu Asn Thr Leu Arg Ala Ala Ile His Ile
        115                 120                 125

Pro Arg Ser Phe Ser His Lys Arg Asp Lys Lys Ile Pro Val Leu Leu
    130                 135                 140

Val Pro Gly Thr Ala Val Pro Ala Ala Ile Thr Phe Tyr Phe Asn Phe
145                 150                 155                 160

Gly Lys Leu Arg Arg Ala Leu Pro Glu Ser Glu Leu Val Trp Ile Asp
                165                 170                 175

Leu Pro Gln Ala Ser Leu Asp Asp Ile Gln Leu Ser Ala Glu Tyr Val
            180                 185                 190

Ala Tyr Ala Leu Asn Tyr Val Ser Ala Leu Thr Ser Ser Lys Ile Ala
        195                 200                 205

Val Ile Ser Trp Ser Gln Gly Ala Leu Asp Ile Gln Trp Ala Leu Lys
    210                 215                 220

Tyr Trp Pro Ser Thr Arg Ser Val Val Asn Asp Phe Ile Ala Ile Ser
225                 230                 235                 240

Pro Asp Phe His Gly Thr Ile Val Lys Trp Leu Val Cys Pro Leu Leu
                245                 250                 255

Asn Asp Leu Ala Cys Thr Pro Ser Ile Trp Gln Gln Gly Trp Asp Ala
            260                 265                 270

Asn Phe Ile Gln Ala Leu Arg Ser Gln Gly Gly Asp Ser Ala Tyr Val
        275                 280                 285

Thr Thr Thr Thr Ile Tyr Ser Ser Phe Asp Lys Ile Val Arg Pro Met
    290                 295                 300

Ser Gly Glu Asn Ala Ser Ala Arg Leu Leu Asp Tyr Arg Gly Val Gly
305                 310                 315                 320

Val Ser Asn Asn His Leu Gln Thr Ile Cys Ala Asn Asn Ala Ala Gly
                325                 330                 335

Gly Leu Tyr Thr His Glu Gly Val Leu Tyr Asn Pro Leu Ala Trp Ala
            340                 345                 350

Leu Thr Val Asp Ala Leu Leu His Asp Gly Pro Ser Asn Ile Thr Arg
        355                 360                 365

Ile Asp Thr Gln Lys Ile Cys Glu Gln Val Leu Pro Pro Tyr Leu Glu
    370                 375                 380

Leu Thr Asp Met Leu Gly Thr Glu Ala Leu Leu Leu Val Ala Leu Ala
385                 390                 395                 400
```

```
Lys Ile Leu Thr Tyr Ser Pro Lys Val Ser Gly Glu Pro Asp Ile Ala
                405                 410                 415

Lys Tyr Ala Tyr
            420

<210> SEQ ID NO 27
<211> LENGTH: 411
<212> TYPE: PRT
<213> ORGANISM: Artificial Sequence
<220> FEATURE:
<223> OTHER INFORMATION: Synthetic

<400> SEQUENCE: 27

Met Ile Phe Thr Ser Ser Pro Ala Val Leu Ser Thr Ile Thr Leu
1               5                   10                  15

Phe Ala Gln Leu Ala Leu Gly Leu Pro Thr Thr Ser Glu Pro Val His
                20                  25                  30

His Glu Ser Val Arg Ala Ile Gly Glu Leu Ser His Arg Asp Glu Leu
            35                  40                  45

His Asp Ala Gly Val Val Trp Asn Lys Val Val Arg Gln Ser Pro Leu
    50                  55                  60

Val Ala Pro Thr Asp Pro Arg Asp Ser Phe Asn Asn Gln Asn Pro Asp
65                  70                  75                  80

Val Pro Gly Val Gly Tyr Pro Arg Ser Asp Ala Asp Pro Ala Phe
                85                  90                  95

Thr Ile Pro Glu Ala Lys Leu Arg Ser Ala Ile Tyr Leu Pro Ser Gly
                100                 105                 110

Phe Asn Ser Ser Thr Asn Arg Gln Val Val Leu Phe Val Pro Gly Thr
            115                 120                 125

Gly Ala Tyr Gly His Glu Ser Phe Ala Asp Asn Leu Leu Lys Val Ile
        130                 135                 140

Thr Asn Ala Gly Ala Ala Asp Ala Val Trp Val Asn Val Pro Asn Ala
145                 150                 155                 160

Met Leu Asp Asp Val Gln Ser Asn Ala Glu Tyr Ile Ala Tyr Ala Ile
                165                 170                 175

Ser Tyr Val Lys Ala Leu Ile Gly Asp Asp Arg Asp Leu Asn Val Ile
                180                 185                 190

Gly Trp Ser Gln Gly Asn Leu Ala Thr Gln Trp Val Leu Thr Tyr Trp
            195                 200                 205

Pro Ser Thr Ala Pro Lys Val Arg Gln Leu Ile Ser Val Ser Pro Asp
    210                 215                 220

Phe His Gly Thr Met Leu Ala Tyr Gly Leu Cys Ala Gly Asn Phe Gly
225                 230                 235                 240

Lys Val Ala Lys Ala Gly Ala Pro Cys Pro Pro Ser Val Leu Gln Gln
                245                 250                 255

Leu Tyr Ser Ser Asn Leu Ile Asn Thr Leu Arg Ala Ala Gly Gly Gly
                260                 265                 270

Asp Ala Gln Val Pro Thr Thr Ser Phe Trp Ser Arg Leu Thr Asp Glu
            275                 280                 285

Val Val Gln Pro Gln Ala Gly Leu Thr Ala Ser Ala Arg Met Gly Asp
    290                 295                 300

Ala Arg Asn Lys Gly Val Thr Asn Val Glu Val Gln Thr Val Cys Gly
305                 310                 315                 320

Leu Ser Val Gly Gly Gln Tyr Gly His Ser Thr Leu Met Ala His
                325                 330                 335
```

-continued

```
Pro Leu Val Ala Ala Met Thr Leu Asp Ala Leu Lys Asn Gly Gly Pro
            340             345             350

Ala Ser Leu Ser Arg Ile Arg Ser Gln Met Phe Arg Ala Cys Ser Asn
        355             360             365

Val Val Ala Pro Gly Leu Gln Leu Thr Asp Arg Ala Lys Thr Glu Gly
    370             375             380

Leu Leu Ala Thr Ala Gly Ala Arg Met Gly Ala Phe Pro Thr Lys Leu
385             390             395             400

Leu Arg Glu Pro Ala Leu Arg Gln Tyr Ala Ala
            405             410
```